(12) United States Patent
Gruber et al.

(10) Patent No.: US 8,025,656 B2
(45) Date of Patent: Sep. 27, 2011

(54) METHODS, SYSTEMS AND DEVICES FOR PERFORMING GYNECOLOGICAL PROCEDURES

(75) Inventors: William Harwick Gruber, Southborough, MA (US); Ronald David Adams, Holliston, MA (US); J. Christopher Flaherty, Topsfield, MA (US)

(73) Assignee: Hologic, Inc., Bedford, MA (US)

( * ) Notice: Subject to any disclaimer, the term of this patent is extended or adjusted under 35 U.S.C. 154(b) by 51 days.

(21) Appl. No.: 11/936,003

(22) Filed: Nov. 6, 2007

(65) Prior Publication Data
US 2008/0135053 A1 Jun. 12, 2008

Related U.S. Application Data

(60) Provisional application No. 60/857,440, filed on Nov. 7, 2006.

(51) Int. Cl.
*A61M 31/00* (2006.01)
(52) U.S. Cl. .......... 604/515; 604/514; 604/517; 604/28; 604/27; 600/114; 606/119; 606/193
(58) Field of Classification Search ............... 604/27, 604/28, 514–515, 517; 600/114; 128/830–831; 128/898; 606/119, 193
See application file for complete search history.

(56) References Cited

U.S. PATENT DOCUMENTS

| | | | |
|---|---|---|---|
| 2,849,002 A | 8/1958 | Oddo et al. | |
| 3,561,429 A | 2/1971 | Jewett et al. | |
| 4,188,952 A | 2/1980 | Loschilov et al. | |
| 4,198,981 A | 4/1980 | Sinnreich | |
| 4,203,444 A | 5/1980 | Bonnell et al. | |
| 4,246,902 A | 1/1981 | Martinez | |
| 4,261,360 A | 4/1981 | Perez | |
| 4,598,698 A | 7/1986 | Siegmund | |
| 4,598,710 A | 7/1986 | Kleinberg et al. | |
| 4,650,462 A | 3/1987 | DeSatnick et al. | |
| 4,673,393 A | 6/1987 | Suzuki et al. | |
| 4,700,694 A | 10/1987 | Shishido | |
| 4,729,763 A | 3/1988 | Henrie | |
| 4,848,323 A | 7/1989 | Marijnissen et al. | |
| 4,895,565 A | 1/1990 | Hillstead | |
| 4,949,718 A | 8/1990 | Neuwirth et al. | |
| 5,078,725 A * | 1/1992 | Enderle et al. ................ 606/193 |
| 5,104,377 A | 4/1992 | Levine | |
| 5,108,414 A | 4/1992 | Enderle et al. | |
| 5,125,903 A | 6/1992 | McLaughlin et al. | |

(Continued)

FOREIGN PATENT DOCUMENTS

EP 0010650 5/1980

(Continued)

OTHER PUBLICATIONS

International Search Report and Written Opinion Received in PCT/US07/83982 Dated May 20, 2008.

(Continued)

*Primary Examiner* — Kevin C Sirmons
*Assistant Examiner* — Edelmira Bosques
(74) *Attorney, Agent, or Firm* — Knobbe Martens Olson & Bear LLP

(57) ABSTRACT

Methods, systems and devices for performing gynecological procedures. According to one embodiment, there is provided a device for accessing the peritoneal cavity of a patient by inserting the device through the vaginal cavity, the cervix, and the uterus and past the fimbria.

8 Claims, 21 Drawing Sheets

U.S. PATENT DOCUMENTS

| | | | |
|---|---|---|---|
| 5,163,433 A | 11/1992 | Kagawa et al. | |
| 5,163,949 A | 11/1992 | Bonutti | |
| 5,183,031 A | 2/1993 | Rossoff | |
| 5,195,541 A | 3/1993 | Obenchain | |
| 5,201,756 A | 4/1993 | Horzewski et al. | |
| 5,222,971 A | 6/1993 | Willard et al. | |
| 5,246,016 A | 9/1993 | Lieber et al. | |
| 5,259,836 A | 11/1993 | Thurmond et al. | |
| 5,269,798 A | 12/1993 | Winkler | |
| 5,275,609 A | 1/1994 | Pingleton et al. | |
| 5,320,091 A | 6/1994 | Grossi et al. | |
| 5,334,183 A | 8/1994 | Wuchinich | |
| 5,361,752 A | 11/1994 | Moll et al. | |
| 5,377,668 A | 1/1995 | Ehmsen et al. | |
| 5,392,765 A | 2/1995 | Muller | |
| 5,402,772 A | 4/1995 | Moll et al. | |
| 5,423,844 A | 6/1995 | Miller | |
| 5,443,470 A | 8/1995 | Stern et al. | |
| 5,450,843 A | 9/1995 | Moll et al. | |
| 5,484,401 A | 1/1996 | Rodriguez et al. | |
| 5,503,626 A | 4/1996 | Goldrath | |
| 5,505,730 A | 4/1996 | Edwards | |
| 5,514,091 A | 5/1996 | Yoon | |
| 5,522,790 A | 6/1996 | Moll et al. | |
| 5,540,658 A | 7/1996 | Evans et al. | |
| 5,575,788 A | 11/1996 | Baker et al. | |
| 5,601,583 A | 2/1997 | Donahue et al. | |
| 5,602,449 A | 2/1997 | Krause et al. | |
| 5,618,296 A | 4/1997 | Sorensen et al. | |
| 5,624,395 A | 4/1997 | Mikhail et al. | |
| 5,624,399 A | 4/1997 | Ackerman | |
| 5,656,013 A | 8/1997 | Yoon | |
| 5,697,940 A | 12/1997 | Chu et al. | |
| 5,709,664 A | 1/1998 | Vandenbroek et al. | |
| 5,725,525 A | 3/1998 | Kordis | |
| 5,730,725 A | 3/1998 | Yoon | |
| 5,738,629 A | 4/1998 | Moll et al. | |
| 5,741,287 A | 4/1998 | Alden et al. | |
| 5,743,850 A | 4/1998 | Moll et al. | |
| 5,743,851 A | 4/1998 | Moll et al. | |
| 5,749,845 A | 5/1998 | Hildebrand et al. | |
| 5,749,889 A | 5/1998 | Bacich et al. | |
| 5,755,731 A | 5/1998 | Grinberg | |
| 5,782,800 A | 7/1998 | Yoon | |
| 5,800,493 A | 9/1998 | Stevens et al. | |
| 5,807,401 A | 9/1998 | Grieshaber et al. | |
| 5,823,945 A | 10/1998 | Moll et al. | |
| 5,843,046 A | 12/1998 | Motisi et al. | |
| 5,855,549 A | 1/1999 | Newman | |
| 5,857,585 A | 1/1999 | Tolkoff et al. | |
| 5,865,728 A | 2/1999 | Moll et al. | |
| 5,873,815 A * | 2/1999 | Kerin et al. | 600/114 |
| 5,891,134 A | 4/1999 | Goble et al. | |
| 5,899,915 A | 5/1999 | Saadat | |
| 5,902,251 A | 5/1999 | VanHooydonk | |
| 5,904,649 A | 5/1999 | Andrese | |
| 5,904,680 A | 5/1999 | Kordis et al. | |
| 5,911,739 A | 6/1999 | Kordis et al. | |
| 5,916,198 A | 6/1999 | Dillow | |
| 5,954,714 A | 9/1999 | Saadat et al. | |
| 5,954,715 A | 9/1999 | Harrington et al. | |
| 5,961,444 A | 10/1999 | Thompson | |
| 5,961,532 A | 10/1999 | Finley et al. | |
| 5,964,755 A | 10/1999 | Edwards | |
| 5,964,777 A | 10/1999 | Drucker | |
| 5,972,000 A | 10/1999 | Beyar et al. | |
| 6,002,968 A | 12/1999 | Edwards | |
| 6,032,673 A | 3/2000 | Savage et al. | |
| 6,039,748 A | 3/2000 | Savage et al. | |
| 6,042,590 A | 3/2000 | Sporri et al. | |
| 6,068,626 A | 5/2000 | Harrington et al. | |
| 6,080,129 A * | 6/2000 | Blaisdell | 604/515 |
| 6,086,544 A | 7/2000 | Hibner et al. | |
| 6,117,070 A | 9/2000 | Akiba | |
| 6,126,635 A | 10/2000 | Simpson et al. | |
| 6,139,570 A | 10/2000 | Saadat et al. | |
| 6,149,632 A | 11/2000 | Landuyt | |
| 6,159,209 A | 12/2000 | Hakky | |
| 6,190,357 B1 | 2/2001 | Ferrarl et al. | |
| 6,216,043 B1 | 4/2001 | Swanson et al. | |
| 6,216,044 B1 | 4/2001 | Kordis | |
| 6,221,007 B1 | 4/2001 | Green | |
| 6,293,952 B1 | 9/2001 | Brosens et al. | |
| 6,319,272 B1 | 11/2001 | Brenneman et al. | |
| 6,328,686 B1 | 12/2001 | Kovac | |
| 6,378,524 B1 * | 4/2002 | Jones | 128/830 |
| 6,387,110 B1 | 5/2002 | Drucker et al. | |
| 6,395,012 B1 | 5/2002 | Yoon et al. | |
| 6,428,498 B2 | 8/2002 | Uflacker | |
| 6,432,116 B1 | 8/2002 | Callister et al. | |
| 6,440,061 B1 | 8/2002 | Wenner et al. | |
| 6,458,076 B1 | 10/2002 | Pruitt | |
| 6,471,644 B1 | 10/2002 | Sidor, Jr. | |
| 6,494,909 B2 | 12/2002 | Greenhalgh | |
| 6,537,207 B1 | 3/2003 | Rice et al. | |
| 6,565,557 B1 | 5/2003 | Sporri et al. | |
| 6,605,037 B1 | 8/2003 | Moll et al. | |
| 6,607,545 B2 | 8/2003 | Kammerer et al. | |
| 6,612,977 B2 | 9/2003 | Staskin et al. | |
| 6,626,940 B2 | 9/2003 | Crowley | |
| 6,638,235 B2 | 10/2003 | Miller et al. | |
| 6,673,101 B1 | 1/2004 | Fitzgerald et al. | |
| 6,682,477 B2 | 1/2004 | Boebel et al. | |
| 6,709,667 B1 | 3/2004 | Lowe et al. | |
| 6,742,236 B1 | 6/2004 | Dion et al. | |
| 6,763,833 B1 | 7/2004 | Khera et al. | |
| 6,802,825 B2 | 10/2004 | Ackerman et al. | |
| 6,805,131 B2 | 10/2004 | Kordis | |
| 6,812,204 B1 | 11/2004 | McHale et al. | |
| 6,821,274 B2 | 11/2004 | McHale et al. | |
| 6,827,703 B1 | 12/2004 | Ackerman | |
| 6,858,024 B1 | 2/2005 | Berg et al. | |
| 6,896,682 B1 | 5/2005 | Mcclellan et al. | |
| 6,951,569 B2 | 10/2005 | Nohilly et al. | |
| 6,960,203 B2 | 11/2005 | Xiao et al. | |
| 6,979,332 B2 | 12/2005 | Adams | |
| 6,997,925 B2 | 2/2006 | Maguire et al. | |
| 7,037,321 B2 | 5/2006 | Sachdeva et al. | |
| 7,070,559 B2 | 7/2006 | Adams et al. | |
| 7,105,003 B2 | 9/2006 | Hiltebrandt | |
| 7,150,713 B2 | 12/2006 | Shener et al. | |
| 7,189,206 B2 | 3/2007 | Quick et al. | |
| 7,226,459 B2 | 6/2007 | Cesarini et al. | |
| 7,226,460 B2 | 6/2007 | Gibson et al. | |
| 7,249,602 B1 | 7/2007 | Emanuel | |
| 7,458,940 B2 | 12/2008 | Miller | |
| 7,462,187 B2 | 12/2008 | Johnston et al. | |
| 7,468,060 B2 | 12/2008 | Utley et al. | |
| 7,491,212 B2 | 2/2009 | Sikora et al. | |
| 7,497,833 B2 | 3/2009 | Miller | |
| 7,510,563 B2 | 3/2009 | Cesarini et al. | |
| 7,588,545 B2 | 9/2009 | Cohen et al. | |
| 7,611,474 B2 | 11/2009 | Hibner et al. | |
| 7,666,200 B2 | 2/2010 | Heisler | |
| 7,749,254 B2 | 7/2010 | Sobelman et al. | |
| 7,753,857 B2 | 7/2010 | Hibner | |
| 7,763,033 B2 * | 7/2010 | Gruber et al. | 606/119 |
| 7,785,250 B2 | 8/2010 | Nakao | |
| 7,806,835 B2 | 10/2010 | Hibner et al. | |
| 7,938,804 B2 | 5/2011 | Fischvogt | |
| 2001/0008575 A1 | 7/2001 | Rho et al. | |
| 2001/0029371 A1 | 10/2001 | Kordis | |
| 2001/0041900 A1 | 11/2001 | Callister et al. | |
| 2001/0047183 A1 | 11/2001 | Privitera et al. | |
| 2001/0056222 A1 | 12/2001 | Rudischhauser et al. | |
| 2002/0010457 A1 | 1/2002 | Duchon et al. | |
| 2002/0013601 A1 | 1/2002 | Nobles et al. | |
| 2002/0020417 A1 | 2/2002 | Nikolchev et al. | |
| 2002/0068934 A1 | 6/2002 | Edwards et al. | |
| 2002/0082634 A1 | 6/2002 | Kammerer et al. | |
| 2003/0050639 A1 | 3/2003 | Yachia et al. | |
| 2003/0083684 A1 | 5/2003 | Cesarini et al. | |
| 2003/0114875 A1 | 6/2003 | Sjostrom | |
| 2003/0153940 A1 | 8/2003 | Nohilly et al. | |
| 2004/0002702 A1 | 1/2004 | Xiao et al. | |
| 2004/0002703 A1 | 1/2004 | Xiao et al. | |
| 2004/0049211 A1 | 3/2004 | Tremulis et al. | |

| | | |
|---|---|---|
| 2004/0116955 A1 | 6/2004 | Foltz et al. |
| 2004/0127932 A1 | 7/2004 | Shah |
| 2004/0204682 A1 | 10/2004 | Smith |
| 2004/0225187 A1 | 11/2004 | Kamrava et al. |
| 2004/0255957 A1 | 12/2004 | Cafferata |
| 2004/0267157 A1 | 12/2004 | Miller et al. |
| 2005/0027245 A1 | 2/2005 | Sachdeva et al. |
| 2005/0045183 A1 | 3/2005 | Callister et al. |
| 2005/0080318 A1 | 4/2005 | Squicciarini |
| 2005/0090849 A1 | 4/2005 | Adams |
| 2005/0107663 A1 | 5/2005 | Saadat et al. |
| 2005/0113715 A1 | 5/2005 | Schwindt et al. |
| 2005/0113836 A1 | 5/2005 | Lozier et al. |
| 2005/0113857 A1 | 5/2005 | Nohilly et al. |
| 2005/0177168 A1 | 8/2005 | Brunnett et al. |
| 2005/0182397 A1 | 8/2005 | Ryan |
| 2005/0222598 A1 | 10/2005 | Ho et al. |
| 2005/0234437 A1 | 10/2005 | Baxter et al. |
| 2005/0240206 A1 | 10/2005 | Sjostrom |
| 2005/0245960 A1 | 11/2005 | Grundeman |
| 2005/0250933 A1 | 11/2005 | Binz et al. |
| 2005/0250993 A1 | 11/2005 | Jaeger |
| 2005/0267408 A1 | 12/2005 | Grandt et al. |
| 2005/0277970 A1 | 12/2005 | Norman et al. |
| 2005/0277975 A1 | 12/2005 | Saadat et al. |
| 2005/0288551 A1 | 12/2005 | Callister et al. |
| 2006/0004436 A1 | 1/2006 | Amarant et al. |
| 2006/0009798 A1 | 1/2006 | Callister et al. |
| 2006/0036138 A1 | 2/2006 | Heller et al. |
| 2006/0047185 A1 | 3/2006 | Shener et al. |
| 2006/0064074 A1 | 3/2006 | Mallaby |
| 2006/0089658 A1 | 4/2006 | Harrington |
| 2006/0189972 A1 | 8/2006 | Grossman |
| 2006/0200042 A1 | 9/2006 | Weikel, Jr. et al. |
| 2006/0206136 A1 | 9/2006 | Sachdeva et al. |
| 2006/0212055 A1 | 9/2006 | Karabey et al. |
| 2006/0241344 A1 | 10/2006 | Wilk |
| 2006/0241586 A1 | 10/2006 | Wilk |
| 2006/0241630 A1 | 10/2006 | Brunnett et al. |
| 2006/0293560 A1 | 12/2006 | Nguyen et al. |
| 2007/0010845 A1 | 1/2007 | Gong et al. |
| 2007/0161957 A1 | 7/2007 | Guenther et al. |
| 2007/0225744 A1 | 9/2007 | Nobles et al. |
| 2007/0227544 A1 | 10/2007 | Swann et al. |
| 2007/0232859 A1 | 10/2007 | Secrest et al. |
| 2008/0015621 A1 | 1/2008 | Emanuel |
| 2008/0051758 A1 | 2/2008 | Rioux et al. |
| 2008/0058588 A1 | 3/2008 | Emanuel |
| 2008/0058595 A1 | 3/2008 | Snoke et al. |
| 2008/0065125 A1 | 3/2008 | Olson |
| 2008/0147012 A1 | 6/2008 | Rome |
| 2008/0183192 A1 | 7/2008 | Saal et al. |
| 2008/0234715 A1 | 9/2008 | Pesce et al. |
| 2008/0245371 A1 | 10/2008 | Gruber et al. |
| 2008/0249366 A1 | 10/2008 | Gruber et al. |
| 2008/0249553 A1 | 10/2008 | Gruber et al. |
| 2008/0262302 A1 | 10/2008 | Azarbarzin et al. |
| 2008/0281224 A1 | 11/2008 | Johnson |
| 2008/0319342 A1 | 12/2008 | Shabaz et al. |
| 2009/0005739 A1 | 1/2009 | Hart et al. |
| 2009/0048485 A1 | 2/2009 | Heisler |
| 2009/0054728 A1 | 2/2009 | Trusty |
| 2009/0118699 A1 | 5/2009 | Utley et al. |
| 2009/0137927 A1 | 5/2009 | Miller |
| 2009/0177217 A1 | 7/2009 | Keller |
| 2009/0198149 A1 | 8/2009 | Privitera et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0063360 A1 | 3/2010 | Harrington et al. |
| 2010/0152533 A1 | 6/2010 | Mark |
| 2010/0152758 A1 | 6/2010 | Mark et al. |
| 2010/0152761 A1 | 6/2010 | Mark |
| 2010/0160818 A1 | 6/2010 | Haberstich et al. |
| 2010/0179480 A1 | 7/2010 | Sugiki et al. |
| 2010/0185153 A1 | 7/2010 | Sugiki et al. |
| 2010/0198242 A1 | 8/2010 | Heisler |
| 2010/0274194 A1 | 10/2010 | Sobelman et al. |
| 2010/0312053 A1 | 12/2010 | Larsen |
| 2011/0034943 A1 | 2/2011 | Churchill et al. |

FOREIGN PATENT DOCUMENTS

| | | |
|---|---|---|
| EP | 0044877 | 2/1982 |
| EP | 0141589 | 5/1985 |
| EP | 0366292 | 5/1990 |
| EP | 0449663 | 10/1991 |
| EP | 0531710 | 10/1991 |
| EP | 0539125 | 4/1993 |
| EP | 782427 | 2/1996 |
| EP | 853468 | 5/1996 |
| EP | 0812573 | 12/1997 |
| EP | 1259180 | 9/2001 |
| EP | 1635695 | 1/2005 |
| FR | 2701401 | 8/1994 |
| WO | WO 1994/007445 | 4/1994 |
| WO | WO 1994/011052 | 5/1994 |
| WO | WO 1995/010326 | 4/1995 |
| WO | WO 1995/032011 | 11/1995 |
| WO | WO 1996/015741 | 5/1996 |
| WO | WO 1998/018520 | 5/1998 |
| WO | WO 1998/029068 | 7/1998 |
| WO | WO 1998/051244 | 11/1998 |
| WO | WO 1999/060960 | 12/1999 |
| WO | WO 2000/000100 | 1/2000 |
| WO | WO 2000/012832 | 3/2000 |
| WO | WO 2000/066031 | 11/2000 |
| WO | WO 2001/008575 | 2/2001 |
| WO | WO 2003/037194 | 5/2003 |
| WO | WO 2005/009504 | 2/2005 |
| WO | WO 2005/048862 | 6/2005 |
| WO | WO 2005/074844 | 8/2005 |
| WO | WO 2005/104966 | 11/2005 |
| WO | WO 2009/111717 | 9/2009 |
| WO | WO 2010/127171 | 11/2010 |
| WO | WO 2010/127174 | 11/2010 |

OTHER PUBLICATIONS

International Search Report and Written Opinion Received in PCT/US08/59493 Dated Apr. 4, 2008.
International Search Report and Written Opinion Received in PCT/US07/83833 Dated Jun. 5, 2008.
International Search Report and Written Opinion Received in PCT/US08/59504 Dated Sep. 4, 2008.
International Search Report and Written Opinion Received in PCT/US08/59503 Dated Sep. 5, 2008.
International Search Report and Written Opinion Received in PCT/US07/79449 Dated Jan. 28, 2008.
U.S. Appl. No. 11/852,151, including its prosecution history, and the Office Actions, filed Apr. 24, 2008, Gruber, et al.
U.S. Appl. No. 11/951,853, including its prosecution history, and the Office Actions, filed Oct. 9, 2008, Gruber, et al.
U.S. Appl. No. 11/852,116, including its prosecution history, and the Office Actions, filed Apr. 24, 2008, Gruber, et al.
U.S. Appl. No. 11/852,142, including its prosecution history, and the Office Actions, filed Apr. 24, 2008, Gruber, et al.
U.S. Appl. No. 11/852,121, including its prosecution history, and the Office Actions, filed Apr. 24, 2008, Adams, et al.
U.S. Appl. No. 11/852,200, including its prosecution history, and the Office Actions, filed Apr. 24, 2008, Adams, et al.
U.S. Appl. No. 11/923,357, including its prosecution history, and the Office Actions, filed Jun. 19, 2008, Gruber, et al.
U.S. Appl. No. 11/923,482, including its prosecution history, and the Office Actions, filed Jun. 19, 2008, Gruber, et al.
U.S. Appl. No. 12/432,691, including its prosecution history, and the Office Actions, filed Oct. 29, 2009, Adams et al.
U.S. Appl. No. 12/432,702, including its prosecution history, and the Office Actions, filed Oct. 29, 2009, Chin et al.
U.S. Appl. No. 12/432,686, including its prosecution history, and the Office Actions, filed Oct. 29, 2009, Sullivan et al.
U.S. Appl. No. 12/432,675, including its prosecution history, and the Office Actions, filed Oct. 29, 2009, Churchill et al.

U.S. Appl. No. 12/432,647, including its prosecution history, and the Office Actions, filed Oct. 29, 2009, Litscher et al.
U.S. Appl. No. 12/842,775, filed Mar. 3, 2011, Gruber, et al.
U.S. Appl. No. 12/565,620, filed Apr. 8, 2011, Adams, et al.
U.S. Appl. No. 12/972,223, filed Mar. 31, 2011, Sullivan, et al.
U.S. Appl. No. 12/917,351, filed Feb. 10, 2011, Churchill, et al.
U.S. Appl. No. 12/956,974, filed May 19, 2011, Adams, et al.
International Search Report and Written Opinion dated Jul. 6, 2010, PCT Application No. PCT/US2010/033047 in 1 pages.
International Search Report and Written Opinion dated Jun. 29, 2010, PCT Application No. PCT/US2010/033050 in 1 pages.
International Search Report and Written Opinion dated Jan. 11, 2011, in PCT Application No. PCT/US10/56416 in 1 pages.
"When mechanical dilation is necessary, a few prerequisites can make a difference", OBG Management, Apr. 2009, vol. 21, No. 4, pp. 29-33.
Mark H. Emanuel, "The Intra Uterine Morcellator: A New Hysteroscopic Operating Technique to Remove Intrauterine Polyps and Myomas," Journal of Minimally Invasive Gynecology, vol. 12, pp. 62-66 (2005).[†]

* cited by examiner

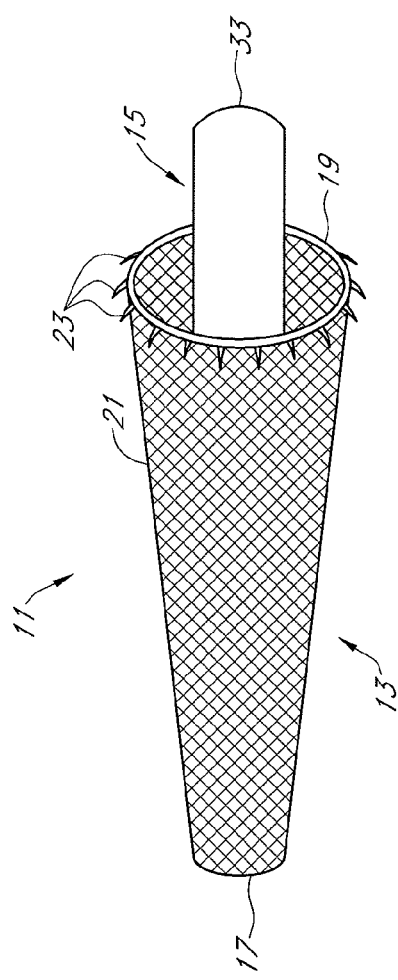
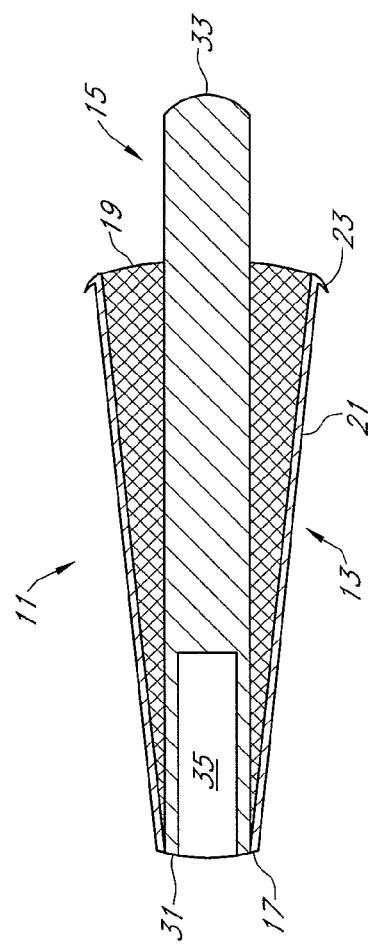
FIG. 1A
FIG. 1B

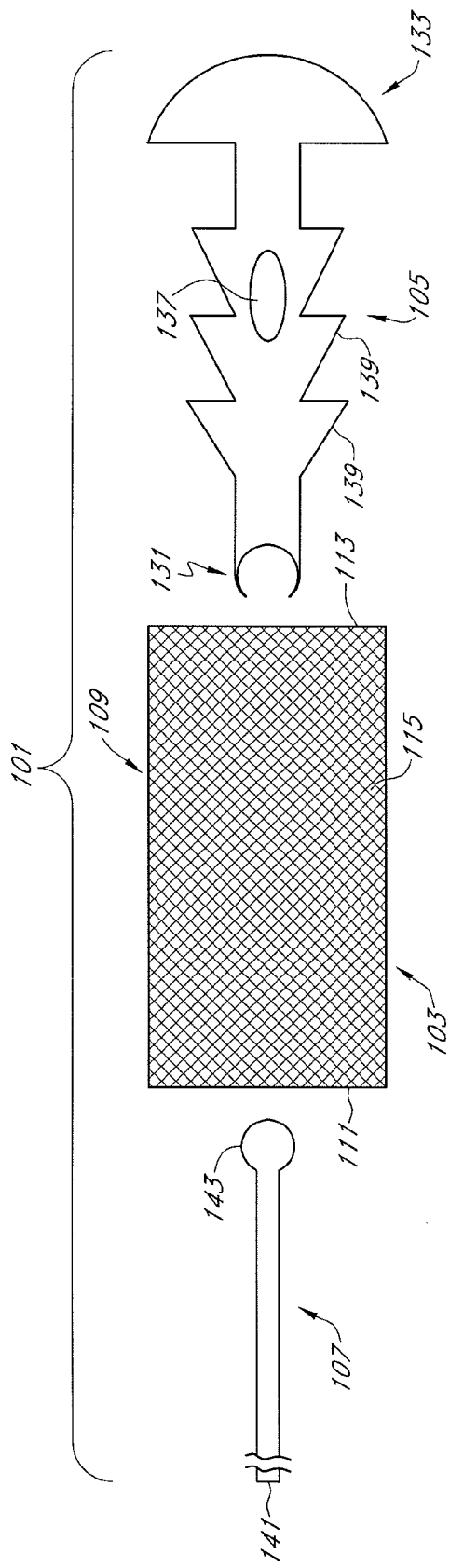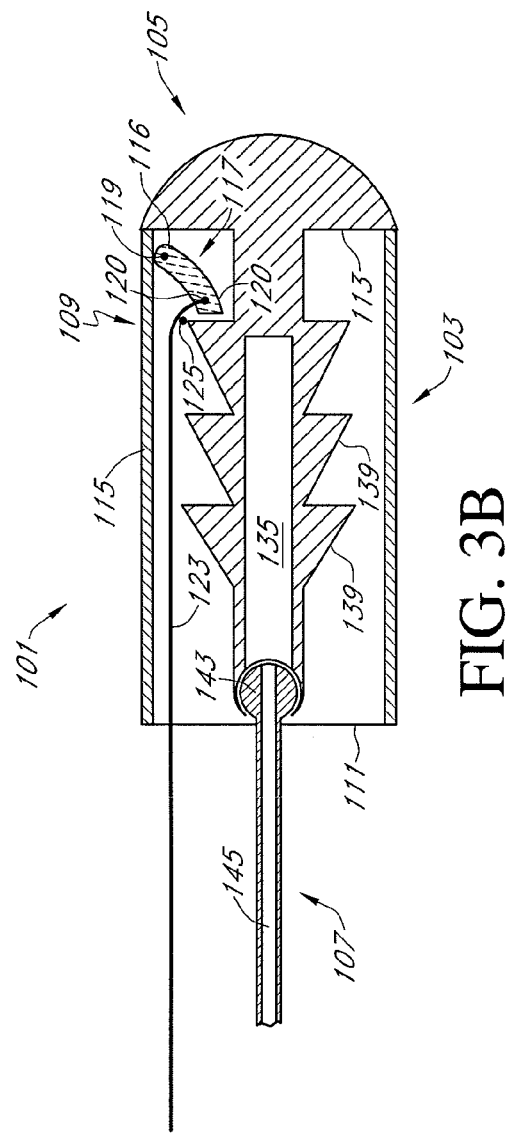
FIG. 3A
FIG. 3B

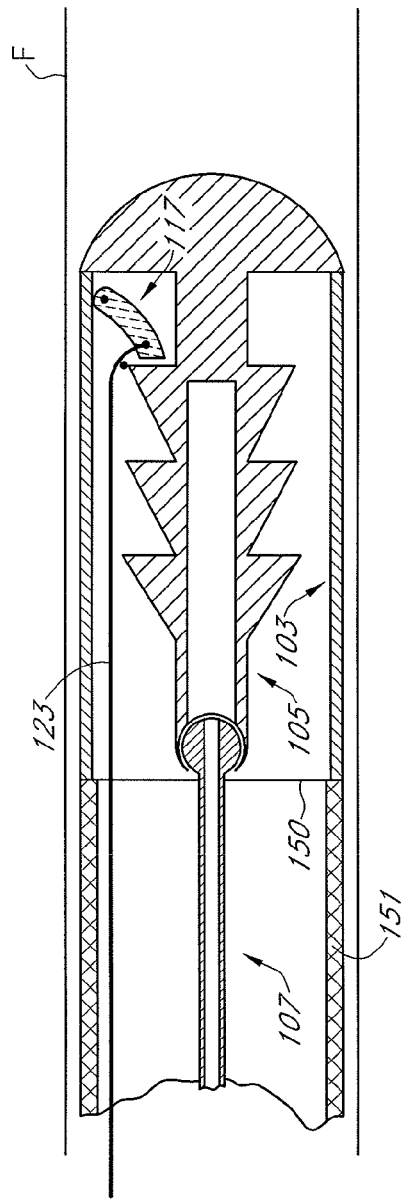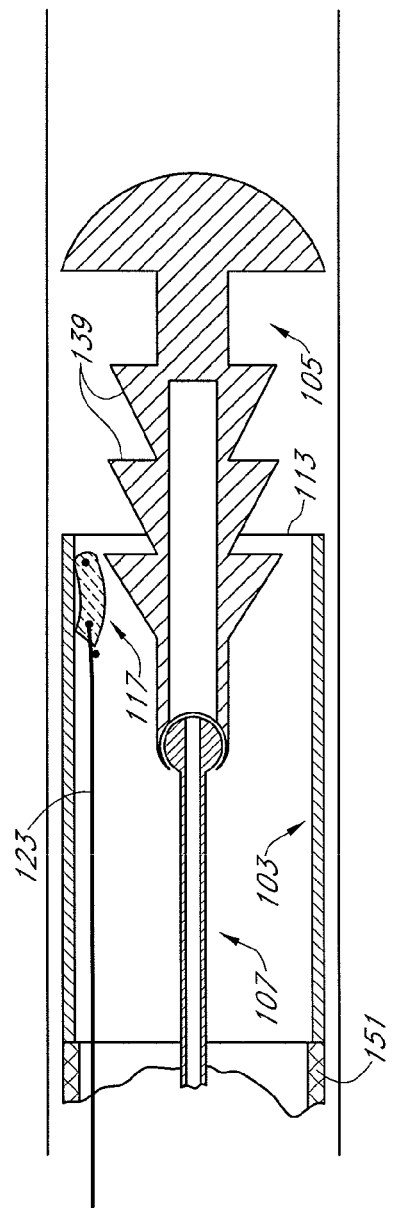
FIG. 4A
FIG. 4B

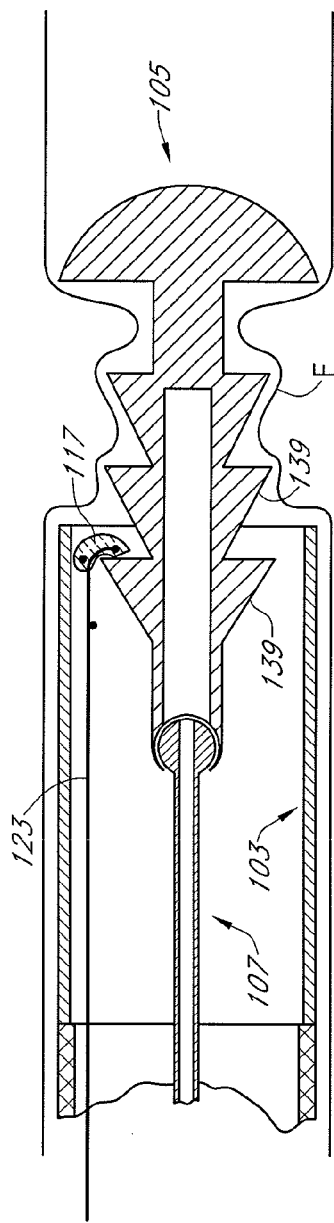
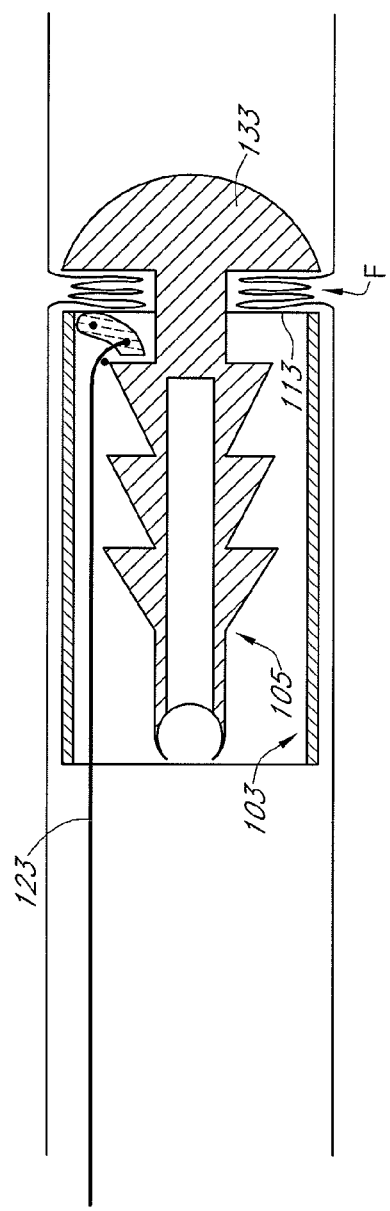
FIG. 4C
FIG. 4D

METHODS, SYSTEMS AND DEVICES FOR PERFORMING GYNECOLOGICAL PROCEDURES

CROSS-REFERENCE TO RELATED APPLICATIONS

The present application claims the benefit under 35 U.S.C. 119(e) of U.S. Provisional Patent Application Ser. No. 60/857,440, filed Nov. 7, 2006, the disclosure of which is incorporated herein by reference.

BACKGROUND OF THE INVENTION

The present invention relates to new methods, systems and devices for performing gynecological procedures.

There are many types of situations when it may be desirable to perform a medical procedure on a patient. The medical procedure may be diagnostic and/or therapeutic in nature. For example, one part of the human anatomy where medical procedures are commonly performed is the female reproductive system. The female reproductive system includes two main parts, the uterus and the ovaries. The uterus is a pear-shaped organ made up of two distinct anatomical regions: the cervix and the corpus. The cervix is a narrow cylindrical passage (about 1.5-4.0 mm in diameter) which connects at its lower end with the vagina. The corpus, which is the portion of the uterus that grows during pregnancy to carry a fetus, is shaped to include two portions: the lower uterine segment and the fundus. The cervix widens at its upper end to form the lower uterine segment of the corpus. The lower uterine segment, in turn, widens at its upper end into the fundus of the corpus. Dimensionally, the length of the uterus, measured from the cervix to the fundus, is approximately 8-10 cm, and the maximum width of the uterus, which is near the fundus, is about 4-5 cm. Extending from the fundus of the uterus on either side are fallopian tubes. The fallopian tubes are continuous with the uterine cavity and allow the passage of an egg from an ovary to the uterus where the egg may implant if fertilized.

One type of commonly-performed gynecological procedure (i.e., a procedure relating to the female reproductive system) is a sterilization procedure, i.e., a procedure intended to prevent future pregnancies. One of the more common types of sterilization procedures has been in the form of "tubal ligation," which has been performed as follows: An appropriately-located incision is made in the patient's abdomen, and a laparoscope is inserted through the incision to provide access to a fallopian tube of the patient. A suture is inserted through the laparoscope and is tied around the fallopian tube in such a manner to cinch shut the fallopian tube, thereby preventing the fertilization of an egg within the tube. Because the inner surface of the fallopian tube is provided with a number of folds, several such sutures are typically used to cinch shut the fallopian tube at a plurality of spaced-apart locations. In addition, it is also common to sever the fallopian tube at a point between each pair of adjacent sutures as a further impediment to the fertilization of an egg. The above-described procedure is typically performed on both fallopian tubes.

One variant of the aforementioned "tubal ligation" procedure involves laparoscopically introducing a hook into the patient and using the hook to pull a portion of the fallopian tube into a hairpin loop. Then, a ligating band is inserted tightly around the looped portion of the tube so as to seal the tube shut. Another variant of "tubal ligation" involves laparoscopically introducing an electrocautery device into the patient and using the electrocautery device to sever the tube and to seal the tube shut.

Unlike the above-described sterilization procedures, all of which involve accessing the fallopian tubes laparoscopically and sealing the tubes shut by means located outside the fallopian tubes, certain recently-developed techniques involve accessing the fallopian tubes hysteroscopically and sealing the tubes shut by occluding the tubes from within. One such approach involves hysteroscopically placing within the fallopian tube a device comprising a self-expanding coil surrounding a fibrous polyester member. The fibrous polyester member induces scarring, i.e., the ingrowth of tissue into the fallopian tube, thereby resulting in occlusion of the fallopian tube. Examples of this type of "tubal occlusion" procedure are disclosed in U.S. Pat. No. 6,684,884, inventors Nikolchev et al., issued Feb. 3, 2004, and U.S. Pat. No. 6,705,323, inventors Nikolchev et al., issued Mar. 16, 2004, both of which are incorporated herein by reference. One modification of the aforementioned "tubal occlusion" procedure involves heating the implanted fibrous polyester member to induce further the ingrowth of tissue into the fallopian tube. An example of this modified procedure is disclosed in U.S. Pat. No. 6,726,682, inventors Harrington et al., issued Apr. 27, 2004, which is incorporated herein by reference.

In addition to the above-described sterilization procedures, many other types of gynecological procedures are commonly performed. Some of these procedures take place outside of the uterine cavity and include the draining of ovarian cysts, the treatment of endometriosis in the peritoneal cavity, and the removal of fibroids on the external surface of the uterus. At present, all of the foregoing types of procedures are typically performed using laparoscopic surgery. As can be appreciated, laparoscopic surgery requires suitable equipment and is typically performed in a hospital setting. As a result, such procedures often bear a large cost due to the setting and the support personnel required.

SUMMARY OF THE INVENTION

It is an object of the present invention to provide new methods, systems and devices for performing gynecological procedures.

According to one aspect of the invention, there is provided a device for use in occluding a fallopian tube, the device comprising (a) a self-expandable structure, the self-expandable structure being insertable into the fallopian tube and, once expanded, being engageable with the inner wall of the fallopian tube; and (b) a sclerosing agent, the sclerosing agent being delivered to the fallopian tube by the self-expandable structure.

More specifically, according to one embodiment, the device may include an outer member and an inner member. The outer member may be a hollow, frusto-conical structure shaped to include an open proximal end, an open distal end, and a side wall. The outer member may be self-expandable such that the distal end is biased radially outwardly. In addition, the side wall may have a porous structure to permit the ingrowth of tissue therethrough. Tines may be provided on the outer surface of the side wall to promote the anchoring of the outer member in a fallopian tube. The inner member, which may be structured to induce scarring, may comprise an elongated fibrous body fixed at its proximal end to the proximal end of the outer member. A bore may extend distally from the proximal end of the inner member to receive a delivery rod.

The inner member, which may have pores or interstices to permit the ingrowth of tissue thereinto, is coated or impregnated with a sclerosing agent.

According to another aspect of the invention, there is provided a system for use in occluding a fallopian tube, the system comprising (a) a device, the device comprising (i) a self-expandable structure, the self-expandable structure being insertable into the fallopian tube and, once expanded, being engageable with the inner wall of the fallopian tube; and (ii) a sclerosing agent, the sclerosing agent being delivered to the fallopian tube by the self-expandable structure; (b) a protective delivery sheath, the device being slidably disposed within the protective delivery sheath; and (c) means for translationally positioning the device relative to the protective delivery sheath.

According to still another aspect of the invention, there is provided a device for use in occluding a fallopian tube, the device comprising (a) a tubular member, the tubular member comprising a proximal end, a distal end and a longitudinal bore; (b) an elongated member, the elongated member comprising a proximal end, a distal end, a bore extending distally from the proximal end, and a port located intermediate to the proximal end and the distal end, the port being in fluid communication with the bore, the distal end being enlarged, the proximal end of the elongated member being slidable within the longitudinal bore of the tubular member.

According to still yet another aspect of the invention, there is provided a device for occluding a tube comprising (a) a tubular member, the tubular member comprising a proximal end, a distal end and a longitudinal bore; (b) a balloon, the balloon being reversibly inflatable and being slidably disposed within the longitudinal bore of the tubular member; (c) a ligating band, the ligating band being mounted around the tubular member; and (d) means for ejecting the ligating band distally from the tubular member.

According to a further aspect of the invention, there is provided a method for accessing the peritoneal cavity of a patient, the method comprising the steps of (a) inserting the distal end of a guidewire through the vagina, the cervix, the uterus, and a fallopian tube and into the peritoneal cavity; and (b) inserting the distal end of a scope distally over the guidewire until the distal end of the scope is positioned in the peritoneal cavity.

According to yet a further aspect of the invention, there is provided a method for performing a gynecological procedure in the peritoneal cavity of a patient, the method comprising the steps of: (a) inserting the distal end of a guidewire through the vagina, the cervix, the uterus, and a fallopian tube and into the peritoneal cavity; (b) inserting the distal end of a scope distally over the guidewire until the distal end of the scope is positioned in the peritoneal cavity; (c) removing the guidewire from the patient and from the scope, thereby leaving the guidewire lumen unoccupied; (d) delivering a tool to the peritoneal cavity through the unoccupied lumen of the scope, the tool having at least one of a diagnostic utility and a therapeutic utility; and (e) using the tool to perform at least one of a diagnostic procedure and a therapeutic procedure in the peritoneal cavity.

According to still yet a further aspect of the invention, there is provided a method for performing a gynecological procedure in the peritoneal cavity of a patient, the method comprising the steps of (a) inserting the distal end of a guidewire through the vagina, the cervix, the uterus, and a fallopian tube and into the peritoneal cavity; (b) inserting the distal end of a scope distally over the guidewire until the distal end of the scope is positioned in the peritoneal cavity; (c) inserting the distal end of the guidewire through one of the uterus and the formix; (d) withdrawing the distal end of the guidewire from the patient through the vagina; (e) delivering a tool to the peritoneal cavity by passing the tool over one of the proximal end of the guidewire and the distal end of the guidewire until the tool is positioned in the peritoneal cavity, the tool having at least one of a diagnostic utility and a therapeutic utility; and (f) using the tool to perform at least one of a diagnostic procedure and a therapeutic procedure.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIGS. 1(a) and 1(b) are perspective and longitudinal section views, respectively, of a first embodiment of a tubal occlusion device constructed according to the teachings of the present invention;

FIGS. 3(a) and 3(b) are exploded side and longitudinal section views, respectively, of a second embodiment of a tubal occlusion device constructed according to the teachings of the present invention;

FIGS. 4(a) through 4(d) are schematic views, partly in section, showing how the tubal occlusion device of FIGS. 3(a) and 3(b) may be used;

DETAILED DESCRIPTION OF THE PREFERRED EMBODIMENT

Figure 2A:
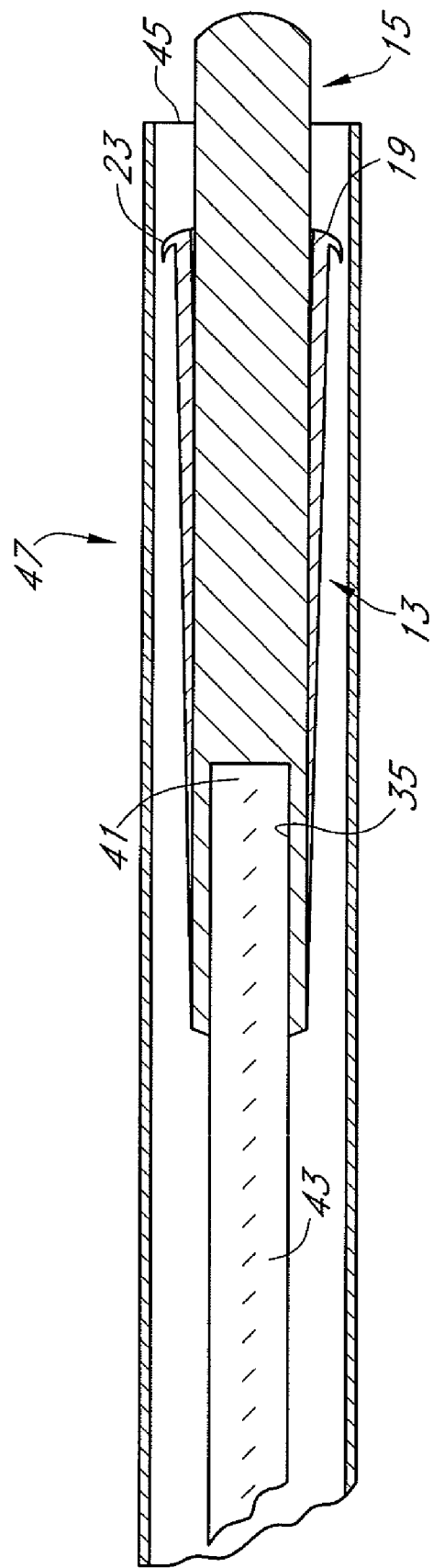
FIGS. 2(a) through 2(d) are schematic views, partly in section, showing how the tubal occlusion device of FIGS. 1(a) and 1(b) may be used.

Referring now to FIGS. 1(a) and 1(b), there are shown perspective and longitudinal section views, respectively, of a first embodiment of an occlusion device for a fallopian tube, the occlusion device being constructed according to the teachings of the present invention and being represented generally by reference numeral 11.

Device 11 may include an outer member 13 and an inner member 15. Outer member 13, which may be a self-expandable structure adapted to engage the inner wall of a fallopian tube, may comprise a hollow, frusto-conical structure shaped to include an open proximal end 17, an open distal end 19, and a side wall 21. Outer member 13 may be made of a resilient or shape-memory material, such as Nitinol (nickel-titanium alloy), so that distal end 19 may be biased radially outwardly. In addition, outer member 13 may be fabricated so that side wall 21 has a mesh structure or other porous structure to permit the ingrowth of tissue therethrough. A plurality of anchoring tines 23 may be provided on the outer surface of side wall 21 proximate to distal end 19, tines 23 being adapted to promote the anchoring of outer member 13 in a fallopian tube wall once outer member 13 has assumed an expanded state therein. Preferably, tines 23 are arranged to take advantage of the peristaltic contractions of the fallopian tube to drive the anchoring members into the intima of the fallopian tube. Thus, as peristalsis tries to expel device 11, tines 23 will be driven into the intima, thereby anchoring device 11 deeper and deeper.

Inner member 15, which may be a structure adapted to induce scarring, may comprise an elongated, cylindrical member shaped to include a proximal end 31 and a distal end 33. Proximal end 31 of inner member 15 may be secured by an adhesive or other suitable means to proximal end 17 of outer member 13. A bore 35 may extend distally from proximal end 31 of inner member 15, bore 35 being adapted to receive a delivery rod or other like structure. Distal end 33, which may extend distally beyond distal end 19 of outer member 13, may be rounded to facilitate the insertion of device 11 into a patient. Inner member 15, which may have pores or interstices to permit the ingrowth of tissue thereinto, may comprise a fibrous polyester member, a mesh metal member or the like and may additionally be coated or impregnated with a sclerosing agent to induce scarring. Examples of suitable sclerosing agents include quinacrine, talc and doxycycline.

Although the dimensions of device 11 may vary, certain exemplary dimensions of outer member 13 may be as follows: length of outer member 13 (i.e., distance from proximal end 17 to distal end 19)—3 cm or less; diameter of proximal end 17—1 mm; diameter of distal end 19 in expanded state—2.0 to 2.5 mm.

Figure 2B:
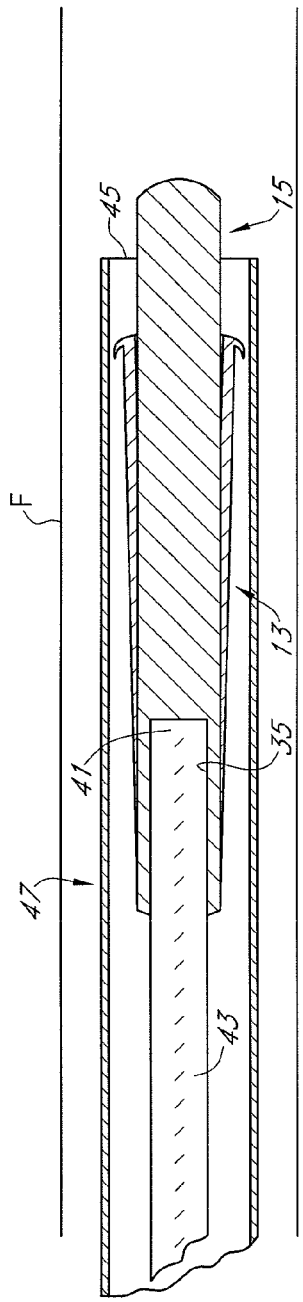
Figure 2C:
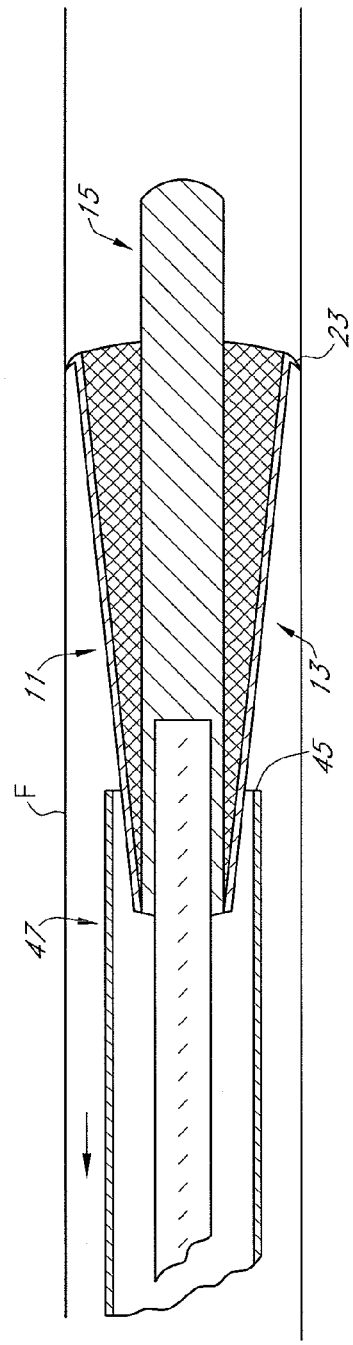
Figure 2D:
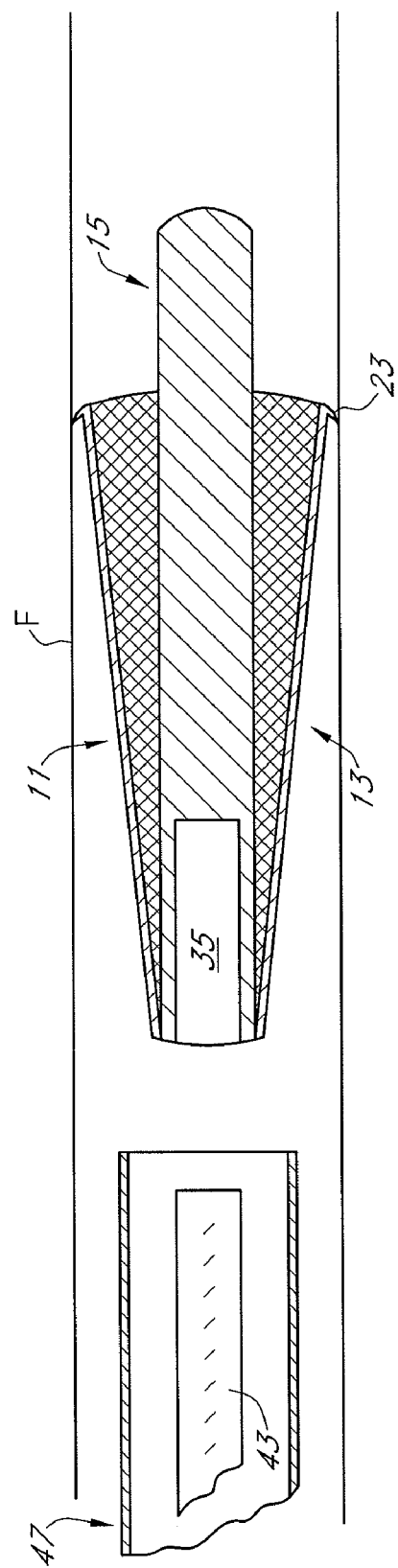
Figure 5:
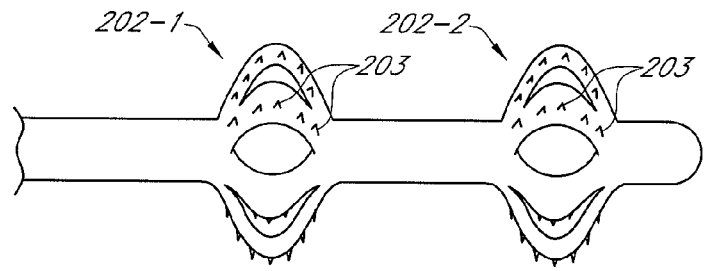
FIG. 5 is a fragmentary side view of a third embodiment of a tubal occlusion device constructed according to the teachings of the present invention.

Referring now to FIGS. 2(a) through 2(d), there is schematically shown one way in which device 11 may be used to occlude a fallopian tube. First, as seen in FIG. 2(a), the distal end 41 of an insertion rod 43 is inserted distally into bore 35 of inner member 15, rod 43 being appropriately dimensioned to engage bore 35 by a friction-fit. (It should be understood that, instead of a friction-fit, rod 43 may be detachably engaged with inner member 15 by other mechanisms, such as a ball-detent mechanism.) Next, the distal end 45 of an outer sheath 47 is inserted over outer member 13 of device 11, sheath 47 being constructed to radially compress distal end 19 of outer member 13 sufficiently to permit transcervical delivery of device 11 to the fallopian tube. Next, as seen in FIG. 2(b), the combination of device 11, distal end 41 of insertion rod 43, and distal end 45 of sheath 47 is inserted into a fallopian tube F of a patient, preferably having been inserted along a vaginal-cervical-uterine pathway. Next, as seen in FIG. 2(c), sheath 47 is retracted proximally from device 11, thereby allowing outer member 13 to self-expand and causing tines 23 to engage fallopian tube F. Finally, as seen in FIG. 2(d), rod 43 is pulled away from device 11, and the combination of rod 43 and sheath 47 is withdrawn from the patient, leaving device 11 secured within fallopian tube F. Although not shown, due to scarring caused by device 11 and by the presence of the sclerosing agent on inner member 15, the tissue on the inner surface of fallopian tube F will, over time, grow into and around device 11, thereby effectively occluding fallopian tube F.

Referring now to FIGS. 3(a) and 3(b), there are shown exploded side and longitudinal section views, respectively, of a second embodiment of an occlusion device for a fallopian tube, the occlusion device being constructed according to the teachings of the present invention and being represented generally by reference numeral 101.

Device 101 may comprise a first portion 103, a second portion 105, and a third portion 107. First portion 103 may comprise a tube 109. Tube 109, which may be appropriately dimensioned to be inserted coaxially into a fallopian tube, may be shaped to include an open proximal end 111, an open distal end 113 and a side wall 115. Side wall 115, which may be cylindrical in shape, may possess a mesh or other porous structure to permit the ingrowth of tissue therethrough. (For clarity and simplicity, the porosity of side wall 115 is not shown in FIG. 3(b).) A first end 116 of a pawl 117 may be pivotally mounted on a pivot pin 119 on the inner surface of side wall 115 proximate to distal end 113. A second end 120 of pawl 117 may be fixed to a distal end 121 of a tensioning cable 123 used to pivot pawl 117, with tensioning cable 123 also being drawn around a pin 125.

Second portion 105 of device 101 may comprise an elongated member shaped to include a proximal end 131 and a distal end 133. Proximal end 131 may have a concave shape for receiving the distal end of third portion 107 in a snap-fit. Distal end 133 may be in the shape of a dome or other enlarged structure preferably at least as large in diameter as first portion 103. Distal end 133 may be coated or impregnated with a sclerosing agent to induce scarring. Examples of suitable sclerosing agents include quinacrine, talc and doxycycline. A bore 135 may extend longitudinally from proximal end 131 to a port 137, port 137 being located at an intermediate point along the length of second portion 105. As will be discussed further below, port 137 is used to apply vacuum pressure so that, when device 101 is inserted into a fallopian tube, the fallopian tube may be pulled radially inwardly. A series of barbs 139 may be provided along the length of second portion, barbs 139 being engageable with second end 120 of pawl 117.

Third portion 107 may comprise an elongated tubular member shaped to include a proximal end 141, a distal end 143 and a longitudinal bore 145. Proximal end 141 may be adapted to be coupled to a source of vacuum pressure. Distal end 143 may have an appropriate shape so that distal end 143 may be coupled to proximal end 131 of second portion 105 by a snap-fit. (It should be understood that, instead of a snap-fit, distal end 143 of third portion 107 and proximal end 131 of second portion 105 may be coupled together in some other detachably engageable manner.)

Although the dimensions of device 101 may vary, the combined length of first portion 103 and second portion 105 (with distal end 133 of second portion 105 lying flush against distal end 113 of first portion 103) may be approximately 30 mm, more preferably approximately 20 mm, even more preferably approximately 10 mm. The outer diameter of device 101, when assembled, may be less than 3 mm, more preferably less than 2 mm, even more preferably less than 1 mm.

Referring now to FIGS. 4(a) through 4(d), there is schematically shown one way in which device 101 may be used to occlude a fallopian tube. First, as seen in FIG. 4(a), with device 101 assembled and mounted on the distal end 150 of a delivery catheter 151, device 101 is inserted into a fallopian tube F of a patient, preferably having been inserted along a vaginal-cervical-uterine pathway. Next, as seen in FIG. 4(b), with tension applied to cable 123 in such a way as to move pawl 117 away from barbs 139, third portion 107 is moved distally until port 137 is positioned distally relative to distal end 113 of first portion 103. As can be seen, this movement of second portion 105 relative to first portion 103 creates a waist or length of narrowed diameter between first portion 103 and distal portion 133 of second portion 105. Next, as seen in FIG. 4(c), tension is released from cable 123, causing pawl 117 to engage barbs 139 and preventing further distal movement of second portion 105 relative to first portion 103. In addition, vacuum pressure is applied to third portion 107, causing fallopian tube F to be drawn radially inwardly towards port 137. Next, as seen in FIG. 4(d), third portion 107 and delivery catheter 151 are withdrawn proximally from the patient. The proximal movement of third portion 107 initially causes second portion 105 to be moved proximally towards first portion 103, resulting in the drawn portion of fallopian tube F being securely clamped between distal end 113 of first portion 103 and distal end 133 of second portion 105. The continued proximal movement of third portion 107 then causes third portion 107 to become disengaged from second portion 105, leaving first portion 103 and second portion 105 secured within fallopian tube F. Although not shown, due to scarring caused by device 101 and by the presence of the sclerosing agent on distal end 133 of second portion 105, the tissue on the inner surface of fallopian tube F will, over time, grow into and around device 101, thereby effectively occluding fallopian tube F.

Figure 6A:
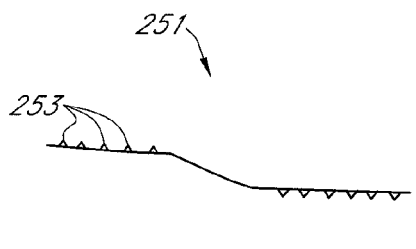
FIGS. 6(a) and 6(b) are side views in a compressed state and in an expanded state, respectively, of a fourth embodiment of a tubal occlusion device constructed according to the teachings of the present invention.
Figure 6B:
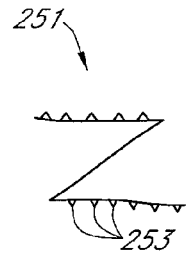
Figure 7:
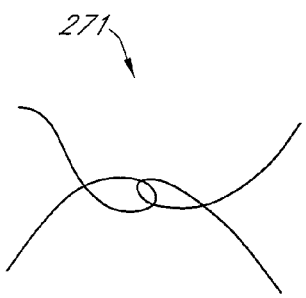
FIG. 7 is a side view of a fifth embodiment of a tubal occlusion device constructed according to the teachings of the present invention.
Figure 8:
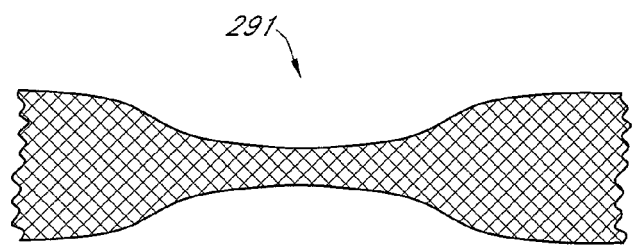
FIG. 8 is a side view of a sixth embodiment of a tubal occlusion device constructed according to the teachings of the present invention.

As can be appreciated, in accordance with the teachings of the present invention, one could use any of a variety of self-expandable structures that have been coated or impregnated with a sclerosing agent as an occlusion device for a fallopian tube. Examples of such coated or impregnated structures are shown in FIGS. 5 through 8. More specifically, in FIG. 5, there is shown a self-expandable device 201 having two malecot structures 202-1 and 202-2 in its expanded state. Barbs 203 may be provided on malecot structures 202-1 and 202-2 to improve the anchoring of device 201 within a fallopian tube. It should be understood that, although two malecot structures are shown in device 201, device 201 could be modified to have as few as one malecot structure or to include three or more malecot structures. Moreover, although the malecot structures of device 201 are aligned with one another, device 201 could be modified by rotating the relative positions of the two malecot structures so that they are staggered relative to one another. In FIGS. 6(a) and 6(b), there is shown a device 251 that may self-expand from a compressed or lower-profile state (FIG. 6(a)) to an expanded or higher-profile Z-shaped state (FIG. 6(b)). Barbs 253 may be provided on device 251 to improve the anchoring of device 251 within a fallopian tube. In FIG. 7, there is shown a device 271 in the form of a spider filter in its expanded state. In FIG. 8, there is shown a device 291 in the form of a modified wallstent, the modified wallstent being twisted in opposite directions at its two ends and then heat-set in this twisted state. In use, the devices of FIGS. 5 through 8 may be delivered to the fallopian tube along a vaginal-cervical-uterine pathway while in a compressed state within a delivery catheter and then may be ejected distally from the delivery catheter using an ejector rod to self-expand into engagement with the fallopian tube of the patient. Due to scarring caused by the device and by the presence of the sclerosing agent on the device, the tissue on the inner surface of the fallopian tube will, over time, grow radially inwardly, thereby effectively occluding the fallopian tube.

Figure 9:
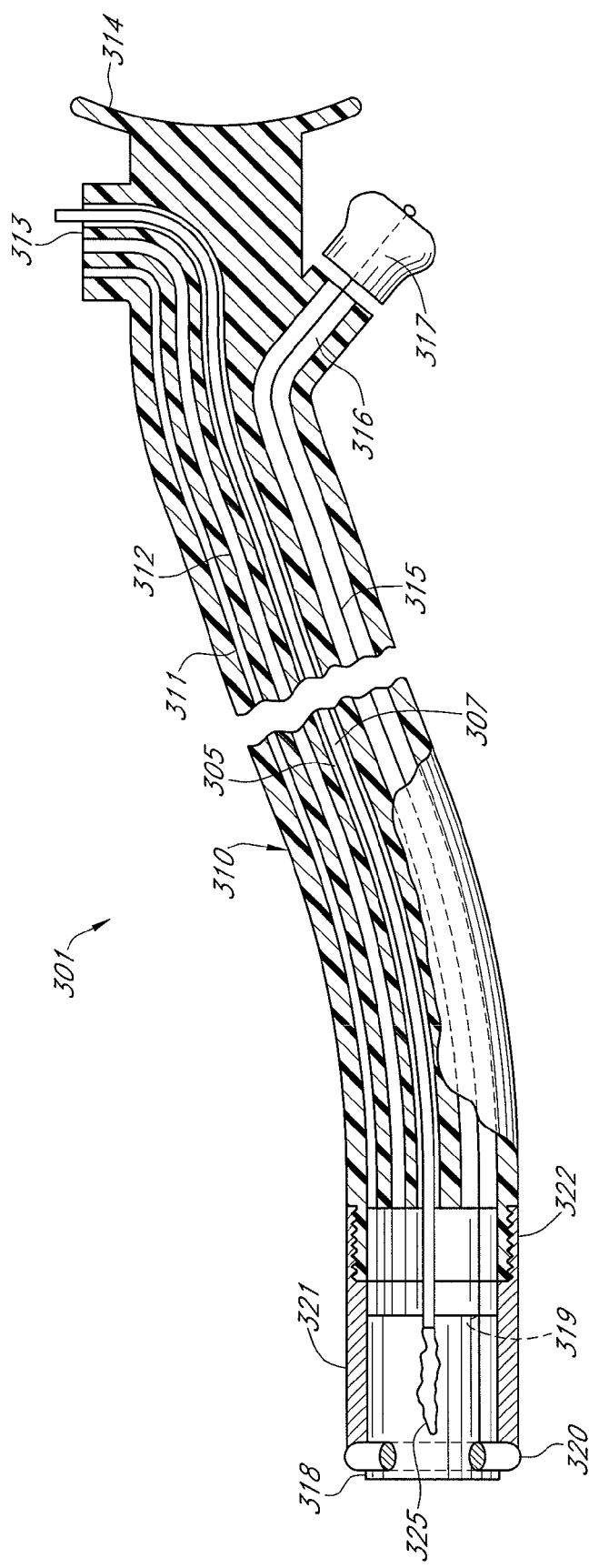
FIG. 9 is a longitudinal section view of a seventh embodiment of a tubal occlusion device constructed according to the teachings of the present invention.

Referring now to FIG. 9, there is shown a longitudinal section view of a seventh embodiment of a tubal occlusion device constructed according to the teachings of the present invention, the tubal occlusion device being represented generally by reference numeral 301.

Device 301, which is similar in certain respects to the device disclosed in U.S. Pat. No. 4,735,194, which is incorporated herein by reference, may include a flexible scope 310 equipped with a suction channel 311 and a fiberoptics illumination channel 312, both exiting at a terminal 313 which may be connected to a control box (not shown) for supplying suction and illumination. In addition, scope 310 may be equipped with a balloon channel 305 for slidably receiving an inflation catheter 307 for a balloon. An eyepiece 314 may provide means for viewing the procedure either directly or by video camera and subsequent projection onto a video monitor. A trip wire 315, located in a channel 316, may be equipped with a weighted handle 317 and may be fastened to an inner tube 318 at a notch 319. A ligating band 320 may be mounted on inner tube 318, which may be positioned within an outer tube 321. Outer tube 321 may be fastened securely to scope 310 by means of a threaded connection 322. An inflatable balloon 325 may be coupled to the distal end of inflation catheter 307, balloon 325 being slidably disposed within inner tube 318.

Figure 10:
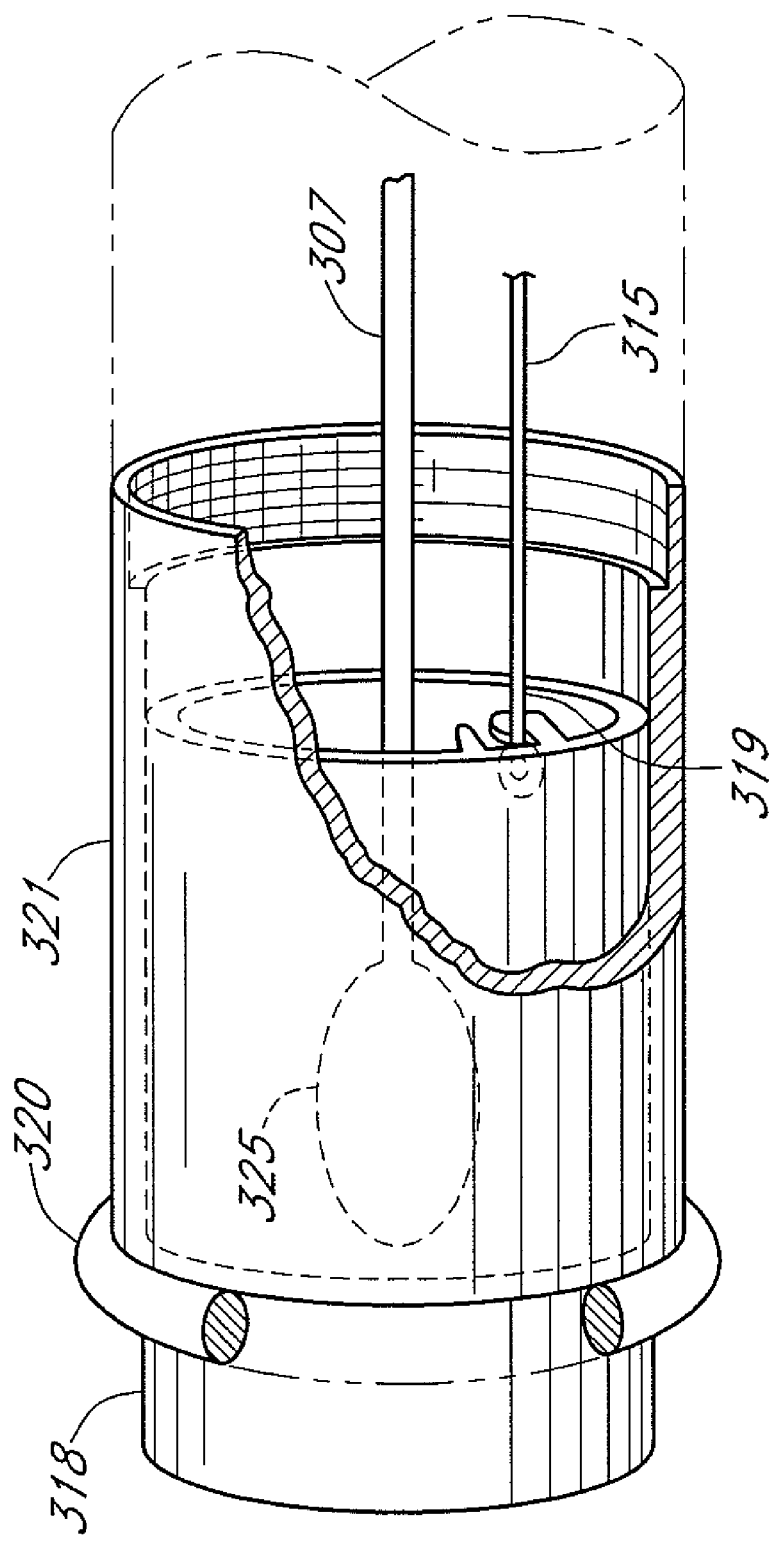
FIG. 10 is an enlarged fragmentary view of the distal end of the device of FIG. 9.

FIG. 10 illustrates in enlarged detail (in phantom) inflatable balloon 325 disposed within inner tube 318. Also illustrated in enlarged detail is ligating band 320 mounted on inner tube 318, which may be inserted within outer tube 321. Trip wire 315 may be secured to notch 319 which provides for the rearward movement of tube 318 that is required to slide band 320 around the tissue to be banded.

In use, the distal end of device 301 may be inserted into the fallopian tube of a patient along the vaginal-cervical-uterine pathway. Next, inflation catheter 307 may be moved distally until balloon 325 (in a deflated state) is positioned distally a short distance beyond the distal end of inner tube 318. Next, balloon 325 may be inflated, balloon 325 preferably engaging the walls of the fallopian tube. (The exterior of balloon 325 may be treated with a sclerosing agent to induce scarring.) Next, with balloon 325 thus inflated, suction may be applied to suction channel 311, such suction causing a portion of the fallopian tube to become invaginated and drawn into inner tube 318. Next, trip wire 315 may be pulled, causing band 320 to slide off inner tube 318 and to become securely fixed around the folded tissue. Next, balloon 325 may be deflated and withdrawn proximally through the banded tissue. Next, device 301 (except for band 320, which is left in place around the folded tissue) may be removed from the patient.

Figure 11:
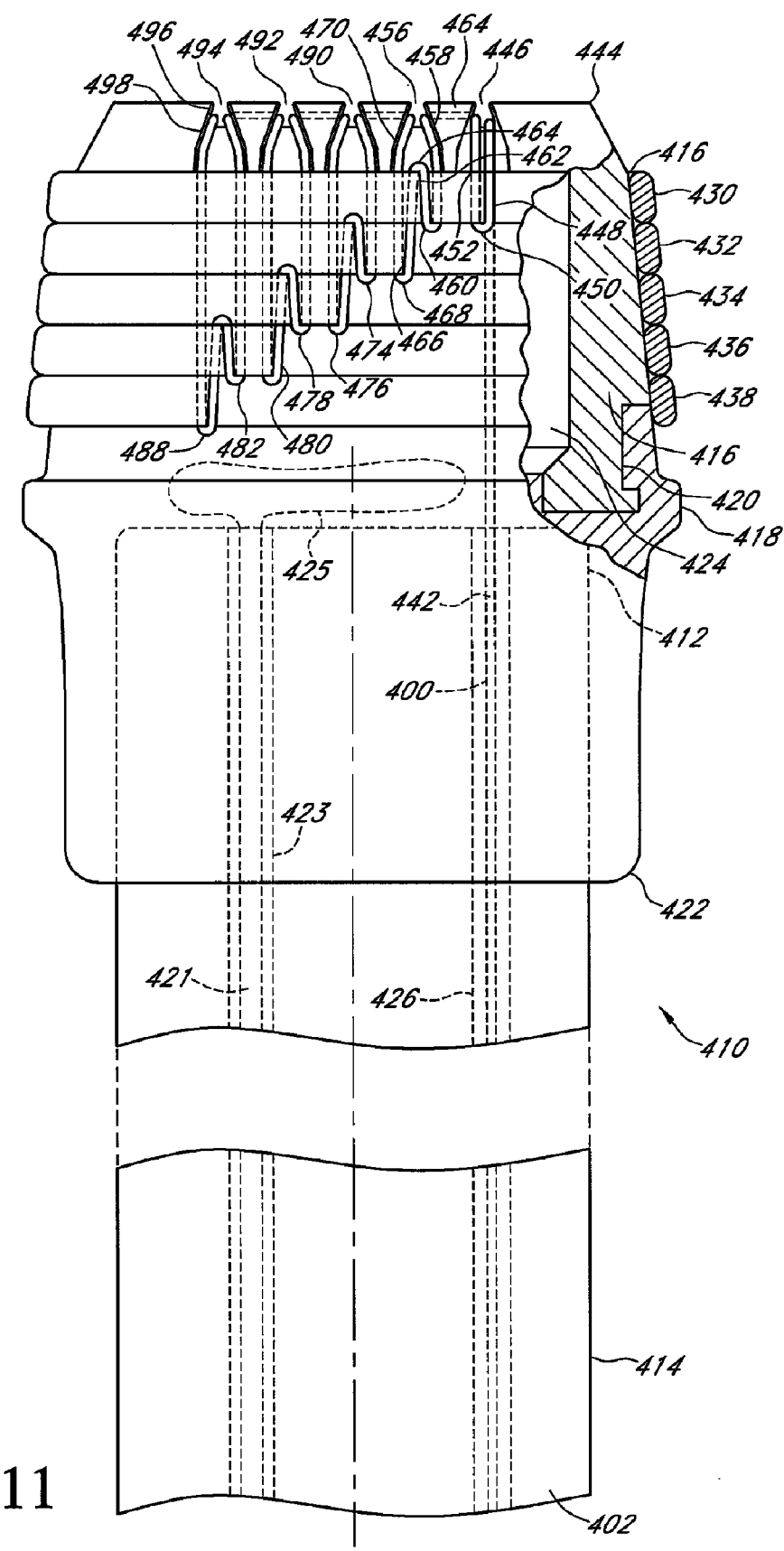
FIG. 11 is a side view, partly in section, of an eighth embodiment of a tubal occlusion device constructed according to the teachings of the present invention.

Whereas device 301 is described above as having a single ligating band, it should be understood that one could provide a similar device capable of dispensing a plurality of ligating bands. An example of such a device is shown in FIG. 11 and is represented generally by reference numeral 410.

Device 410, which is similar in certain respects to the device disclosed in U.S. Pat. No. 5,857,585, which is incorporated herein by reference, is shown attached to the distal end 412 of a scope 414. Device 410 includes a support 416 which engages a flexible connector 418 on a shoulder 420. The other portion 422 of connector 418 attaches to the distal end 412 of scope 414. A passage 424 in support 416 communicates with a lumen 426 in scope 414. A plurality of ligating bands 430, 432, 434, 436 and 438 are stretched onto support 416. The entire assembly of device 410 and scope 414 are typically circularly symmetrical about longitudinal axis 440 and are circular in cross section; however, this is not a necessary feature.

Displacement element 442 extends through passage 424, then lumen 426, and then outwardly over the distal edge 444 of support 416 through notch 446. From there, displacement element 442 loops over at 448, around at 450, and under at 452 the first ligating band 430 and then returns to that same notch 446, extends at 454 along the inside edge and exits radially outwardly once again and exits once again through notch 456, whereupon it moves under 458, around 460 and over 462 the first ligating band 430, then under 464 it moves under 458, around 460 and over 462 the first ligating band 430, then under 464 ligating band 430, over 466 the second ligating band 432, around 468 ligating band 432, and under it 470, back to notch 458. The paths of subsequent loops 474, 476, 478, 480, 482 and 488 and their engagement with notches 490, 492 and 494 can be easily traced. A knot 496 or device of similar function can be placed at the end at 498 of displacement element 442 to prevent it from being pulled through retaining hole 422. Displacement element 442 can be connected to operator element 400 which extends all the way to the proximal end 402 of scope 414. Displacement element 442 and operator element 400 may in fact be one and the same thread, filament, wire or string.

An inflation catheter 421, whose proximal end is adapted to be coupled to an inflation source (not shown), is slidably mounted within a lumen 423 in scope 414. The distal end of inflation catheter 421 is fluidly coupled to an inflatable balloon 425 slidably disposed within passage 424.

In use, the distal end of device 401 is introduced into a fallopian tube through the vaginal-cervical-uterine pathway. Inflatable balloon 425 is then extended distally relative to support 416 and is inflated. Suction is then applied to invaginate a portion of the fallopian tube and to draw the invaginated portion into support 416. Next, displacement element 442 and/or operator element 400 is pulled to the right, causing the first band 430 to be moved and/or rolled to the left toward distal end 444 of support 416. Continued pulling on element 442 and/or 400 causes band 430 to slide free of distal end 444 of support 416. At the moment, the loop 410 of the displacement element 442, being free of notches 446 and 456, will unwrap from around band 430, causing the next pull on element 442 to begin movement of the next band 432. At this time, band 430 collapses about the tissue that has been vacuum-drawn into the end of the support 416. If no further bands are to be dispensed, balloon 425 is then deflated and withdrawn proximally through the banded tissue. If further bands are to be dispensed, movement of element 442 to the right draws up the slack so that further pulling on elements 442 or 400 begins moving band 432 to the left in the same way as band 430. A limiter is provided within support 416 to catch the knot 498 or other device of similar function so that even after the last band 438 is dispensed, element 442 cannot be completely withdrawn from device 410. This serves to keep device 410 tethered to the distal end 412 of scope 414 so that device 410 cannot be inadvertently lost inside the patient. The limiter employs a hole which is smaller than knot 498 so that knot 498 cannot be pulled through it.

As noted above, gynecological procedures are not limited to sterilization procedures. Other common types of gynecological procedures include, for example, the draining of ovarian cysts, the treatment of endometriosis in the peritoneal cavity, and the removal of fibroids on the external surface of the uterus. One feature common to the aforementioned procedures is that such procedures take place outside of the uterine cavity and the fallopian tubes. As noted above, it would be desirable to perform such procedures without having to resort to laparoscopic access through the abdomen.

Figure 12A:
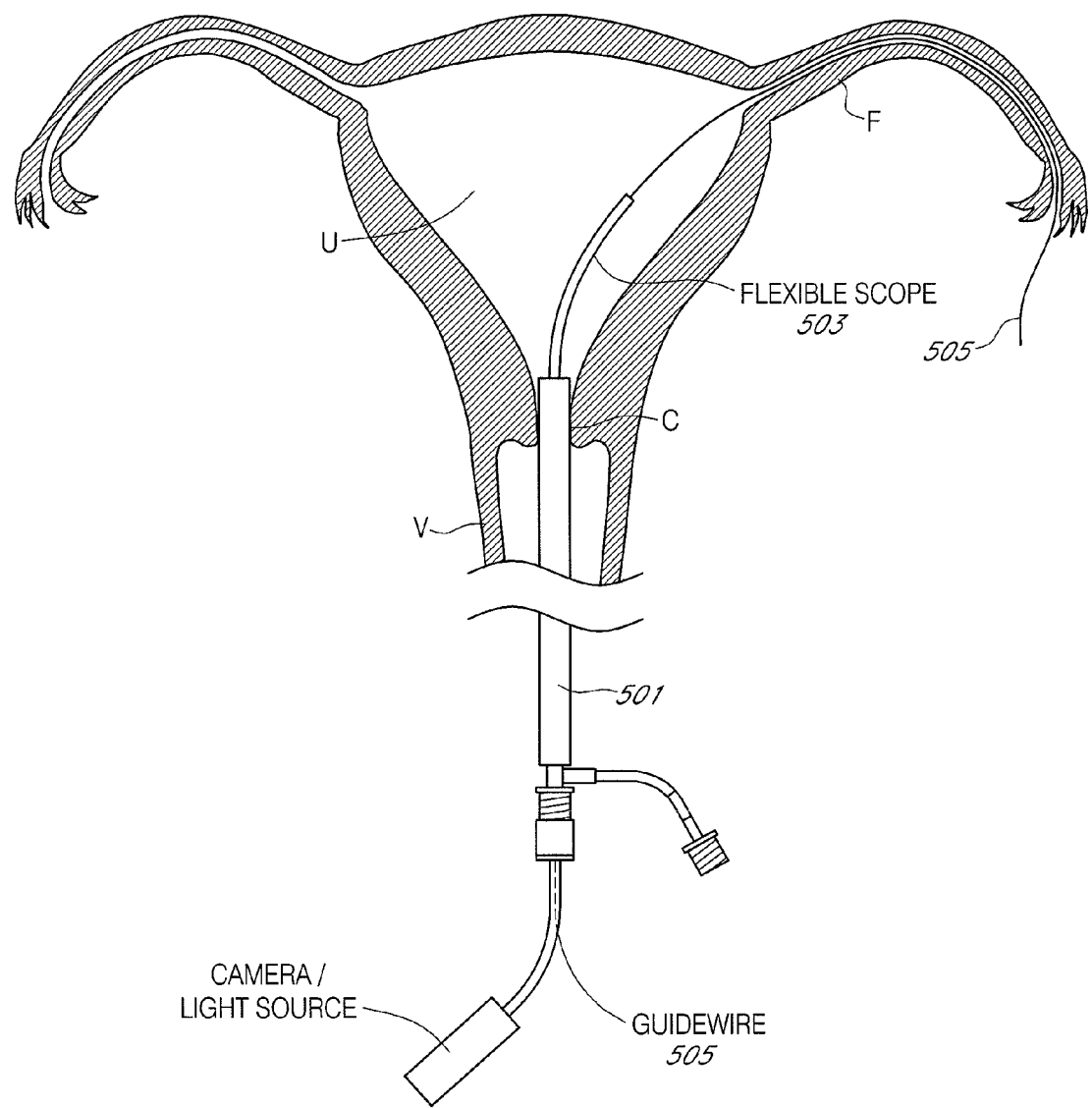
FIGS. 12(a) through 12(c) are schematic diagrams, partly in section, illustrating a first embodiment of a method for performing gynecological procedures in the peritoneal cavity, said method being performed in accordance with the teachings of the present invention.
Figure 12B:
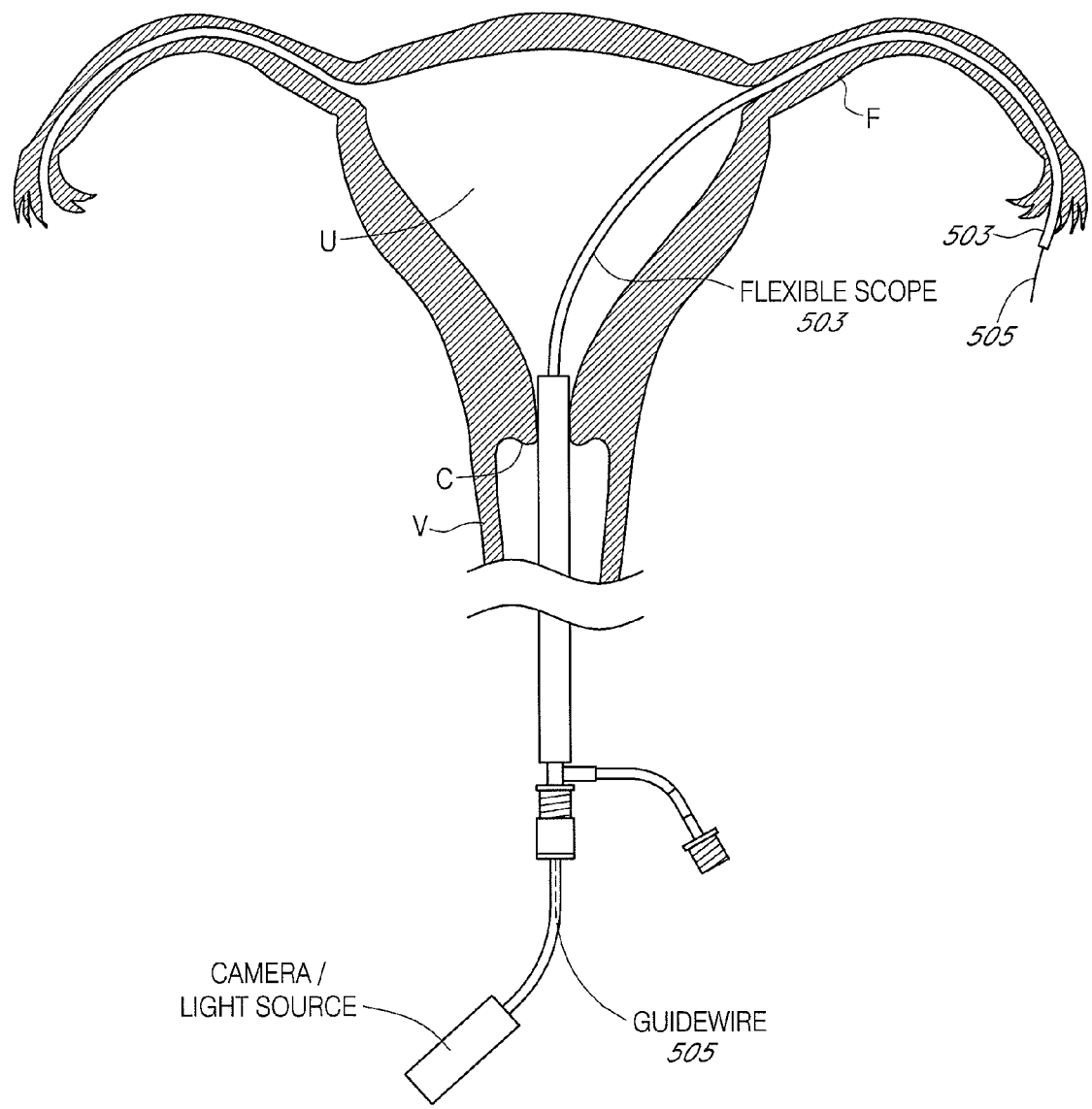
Figure 12C:
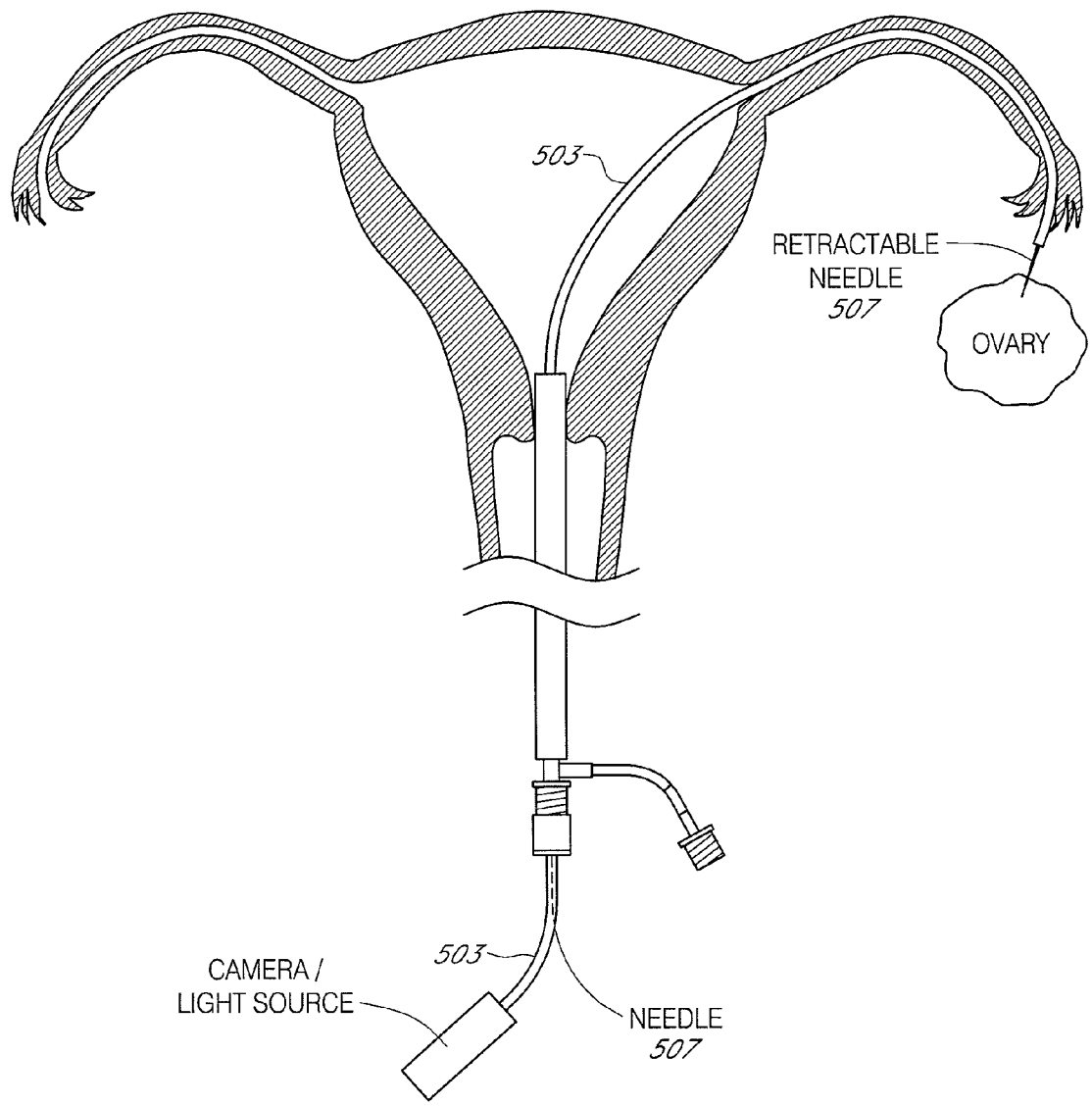
Figure 13A:
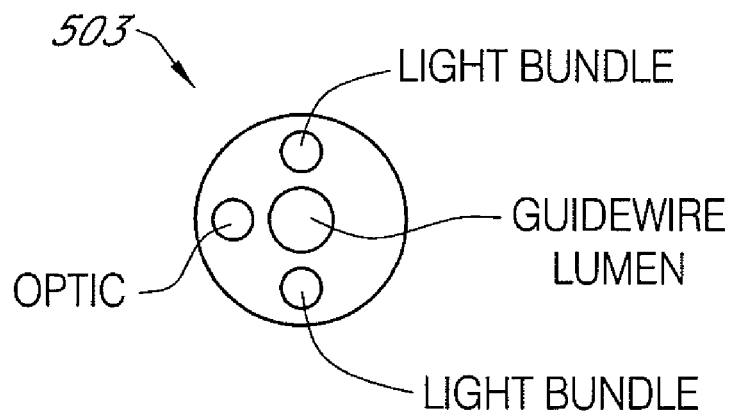
FIG. 13(a) is a section view of the scope shown in FIGS. 12(a) through 12(c)
Figure 13B:
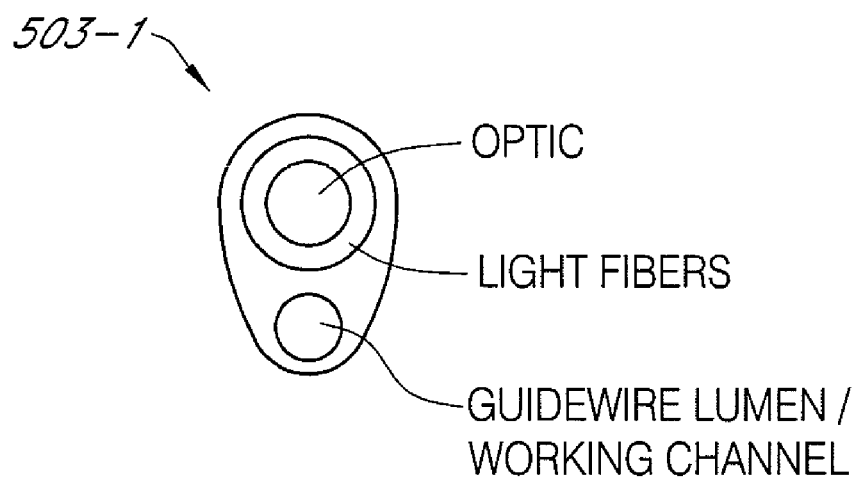
FIG. 13(b) is a section view of an alternate scope suitable for use in the method of FIGS. 12(a) through 12(c), the scope having a teardrop cross-sectional shape.

Referring now to FIGS. 12(a) through 12(c), there are shown schematic diagrams, partly in section, illustrating a new method for performing gynecological procedures in the peritoneal cavity. As seen in FIG. 12(a), this method may first comprise transcervically inserting the distal end of an introducer 501 into a patient, then inserting the distal end of a flexible scope 503 through introducer 501 and into the uterus U of the patient to permit visualization of the fallopian tube F of the patient, and then inserting the distal end of a flexible guidewire 505 through a guidewire lumen in scope 503, across uterus U, through fallopian tube F, past the fimbria, and into the peritoneal cavity. Next, as seen in FIG. 12(b), scope 503 may be advanced distally over guidewire 505 until the distal end of scope 503 is positioned past the fimbria and into the peritoneal cavity. To minimize painful insertion and movement of scope 503 through the fallopian tube, scope 503 preferably has an outer diameter less than about 3 mm, more preferably less than about 2 mm, even more preferably less than about 1 mm. In addition, guidewire 505 and/or scope 503 may be coated with a hydrophilic coating to facilitate their easy passage through the fallopian tube. Next, as seen in FIG. 12(c), guidewire 505 may be withdrawn from the patient, and the distal end of a diagnostic and/or treatment tool 507 may be inserted through the guidewire lumen of scope 503, past the fimbria, and into the peritoneal cavity. In FIG. 12(c), tool 507 is shown as a retractable needle for draining an ovarian cyst. However, tool 507 is not so limited and may include, for example, a laser or RF ablation device, for example, for treating endometriosis, an ultrasound probe for diagnostic purposes, a biopsy forceps, or a morcellator, for example, for treating a fibroid on the exterior of the uterus. The cross-sectional shape of scope 503 may take a circular shape (see FIG. 13(a)) or may take a non-circular shape, such as a teardrop shape (see scope 503-1 of FIG. 13(b)), to allow for the passage of a desired tool 507.

Figure 14A:
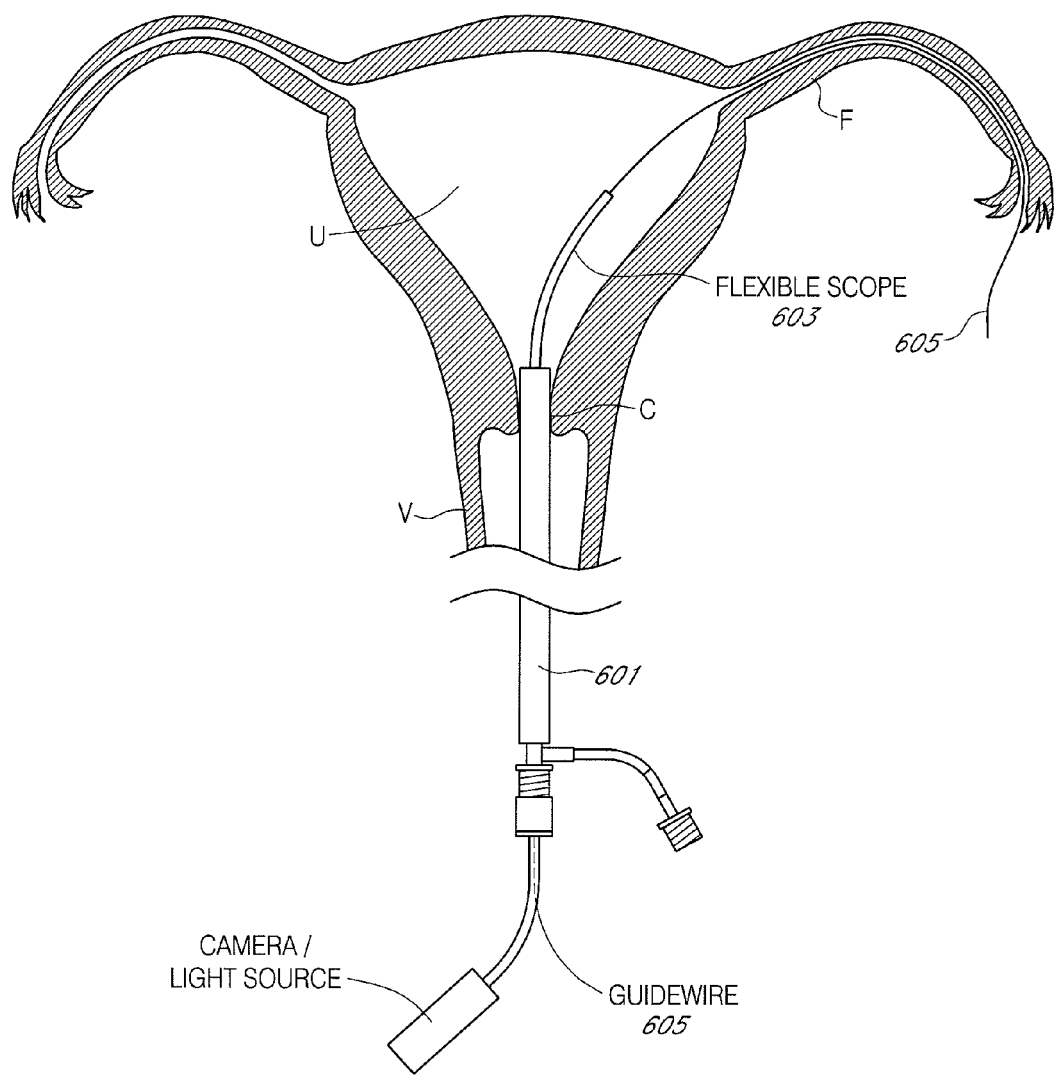
FIGS. 14(a) through 14(d) are schematic diagrams, partly in section, illustrating a second embodiment of a method for performing gynecological procedures in the peritoneal cavity, said method being performed in accordance with the teachings of the present invention.
Figure 14B:
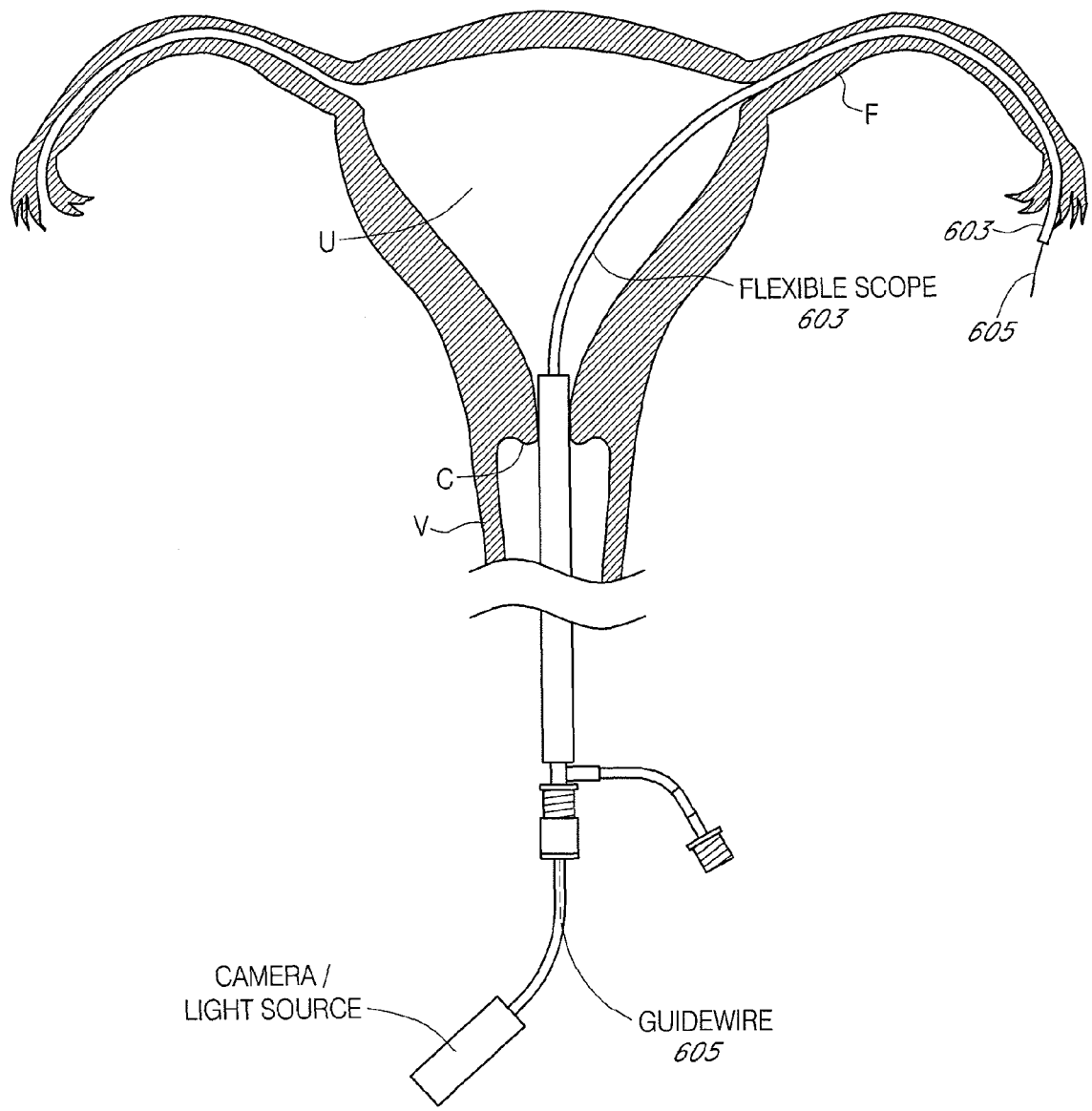
Figure 14C:
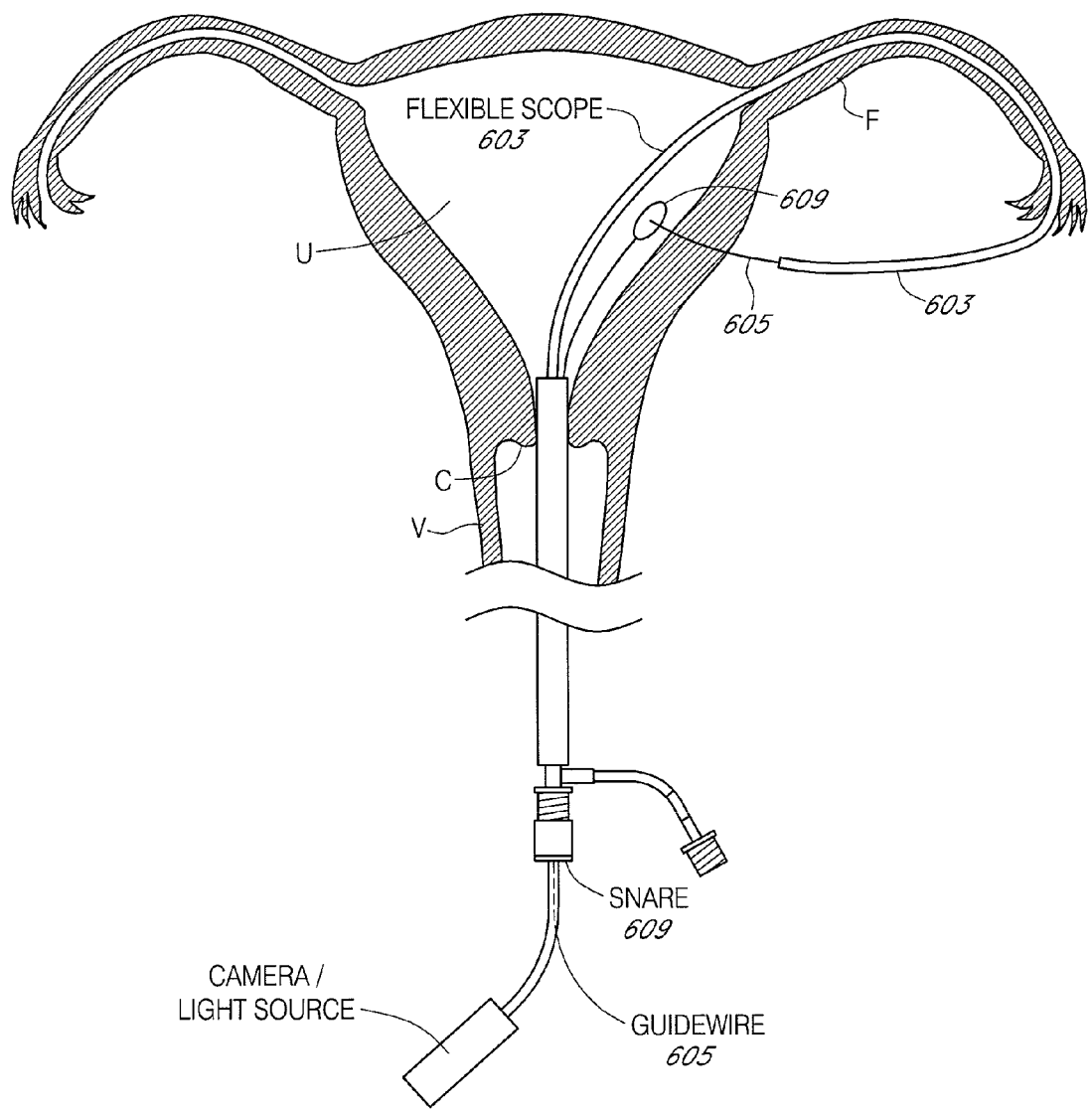
Figure 14D:
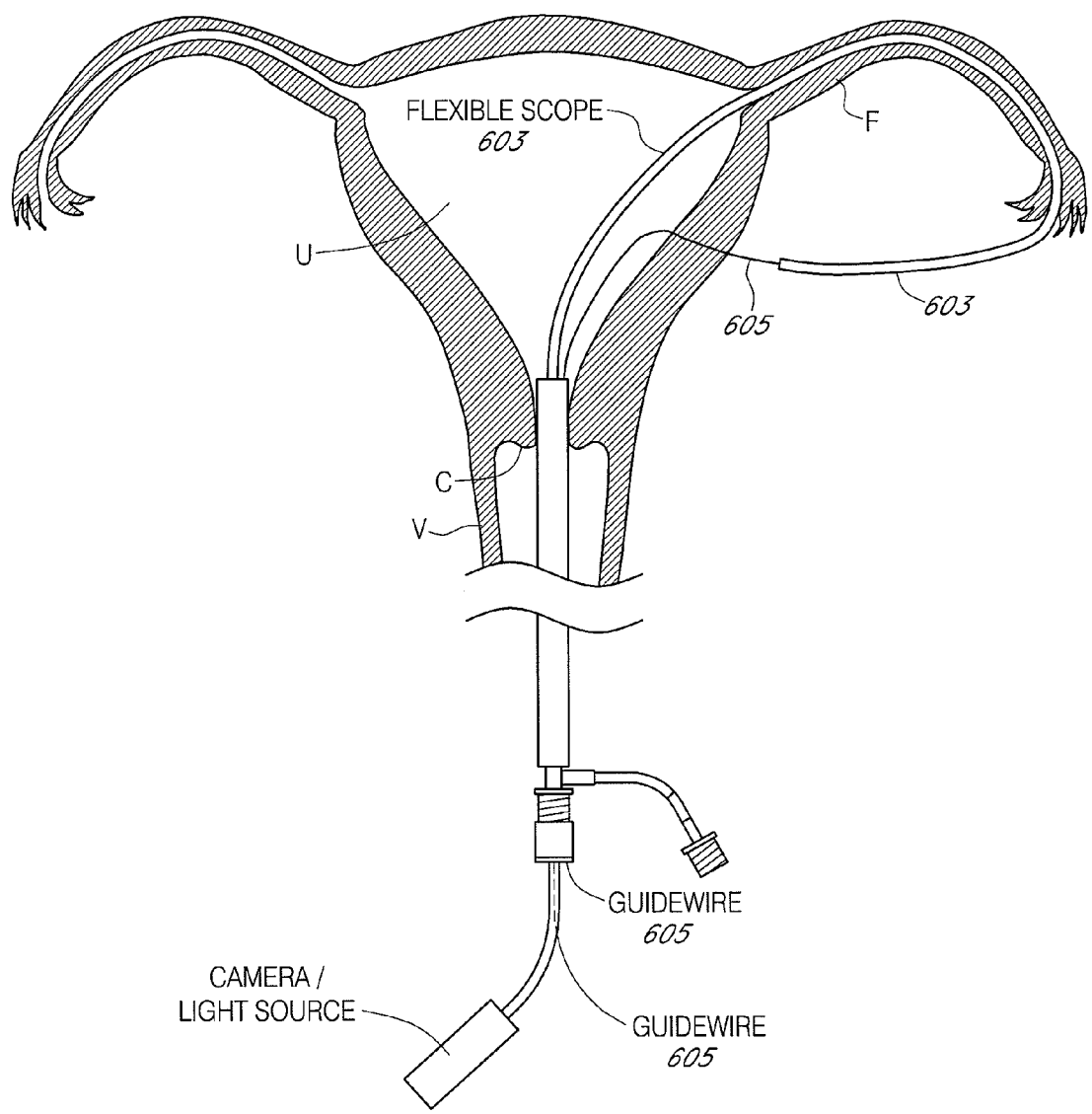
Figure 15:
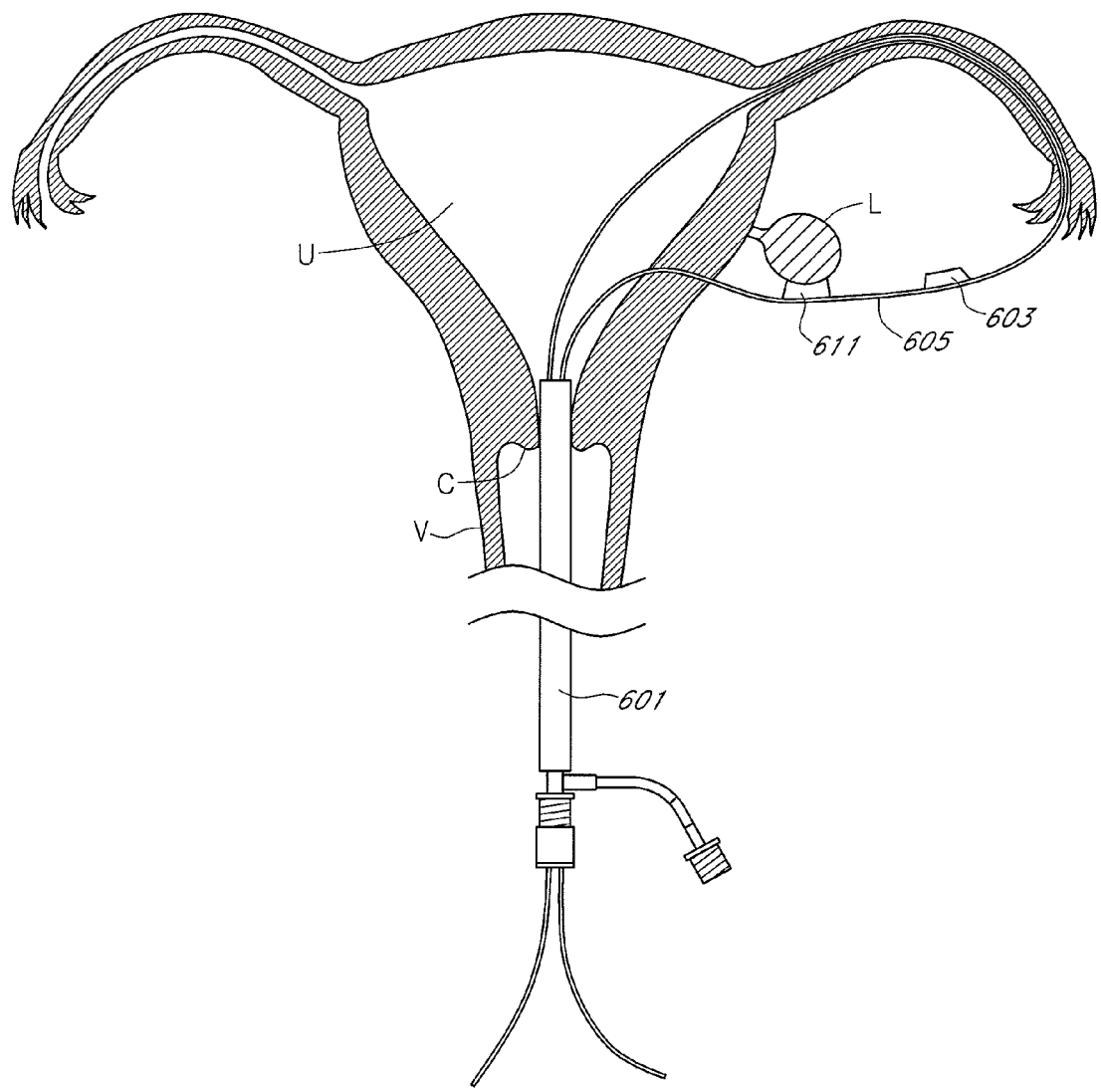
FIG. 15 is a schematic diagram, partly in section, illustrating an application of the method shown in FIGS. 14(a) through 14(d) for treating a fibroid on the exterior surface of the uterus.

Referring now to FIGS. 14(a) through 14(d), there are shown schematic diagrams, partly in section, illustrating another new method for performing gynecological procedures in the peritoneal cavity. As seen in FIG. 14(a), this method may first comprise transcervically inserting the distal end of an introducer 601 into a patient, then inserting the distal end of a flexible scope 603 through introducer 601 and into the uterus U of the patient to permit visualization of the fallopian tube F of the patient, and then inserting the distal end of a flexible guidewire 605 through a guidewire lumen in scope 603, across uterus U, through fallopian tube F, past the fimbria, and into the peritoneal cavity. Next, as seen in FIG. 14(b), scope 603 may be advanced distally over guidewire 605 until the distal end of scope 603 is positioned past the fimbria and into the peritoneal cavity. To minimize painful insertion and movement of scope 603 through the fallopian tube, scope 603 preferably has an outer diameter less than about 3 mm, more preferably less than about 2 mm, even more preferably less than about 1 mm. In addition, guidewire 605 and/or scope 603 may be coated with a hydrophilic coating to facilitate their easy passage through the fallopian tube. Next, as seen in FIG. 14(c), the distal end of guidewire 605 may be inserted through uterus U, where it is then captured by a snare 609. (If desired, the scope 603 may be retracted into the uterus to provide visualization of the capture of the guidewire 605 by snare 609.) Next, as seen in FIG. 14(d), snare 609 and the distal end of guidewire 605 are withdrawn from the patient, thereby creating a guidewire track over which instruments may be passed to desired locations. For example, in FIG. 15, a morcellator 611 is advanced over guidewire 605 and is inserted through the uterine wall into the peritoneal cavity to treat a fibroid located on the exterior surface of the uterus. Other possible applications of the present method include passing a clamp through the fallopian tube using guidewire 605 and then using said clamp to seal shut the fallopian tube.

Figure 16:
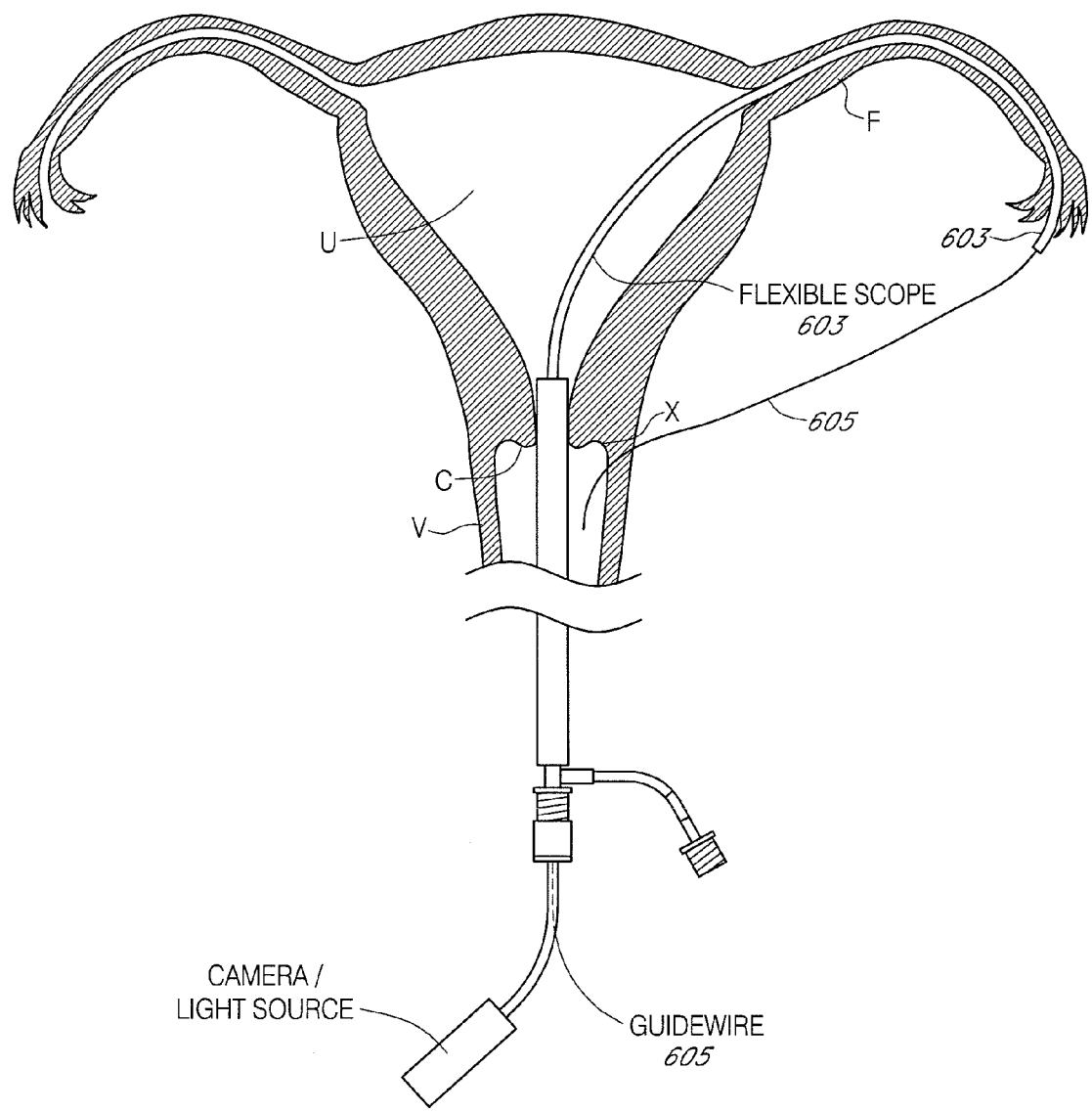
FIG. 16 is a schematic diagram, partly in section, illustrating a variation to the method shown in FIGS. 14(a) through 14(d).

Referring now to FIG. 16, there is shown a schematic diagram, partly in section, illustrating a variation to the method shown in FIGS. 14(a) through 14(d). In FIG. 16, the distal end of guidewire is not passed from the peritoneal cavity through the uterine wall into the uterine cavity, but rather, is passed from the peritoneal cavity through the vaginal fornix X and into the vagina.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method for accessing the peritoneal cavity of a patient, the method comprising the steps of:
   a) inserting the distal end of a guidewire through the vagina, the cervix, the uterus, a fallopian tube, past a fimbria extending from a distal end of the fallopian tube, and into the peritoneal cavity;
   b) inserting the distal end of a scope distally over the guidewire until the distal end of the scope extends past the distal end of the fallopian tube and the fimbria and is positioned in the peritoneal cavity;
   c) directing the distal end of the scope toward a surface within the peritoneal cavity;
   d) removing the guidewire from a guidewire lumen in the scope;
   e) inserting at least a first tool through the guidewire lumen and into the peritoneal cavity, wherein the first tool comprises at least one of a retractable needle configured for draining an ovarian cyst, a laser or RF ablation device configured for treating endometriosis, a biopsy forceps and a morcellator; and
   f) performing a surgical procedure with the first tool, wherein the surgical procedure comprises at least one of draining an ovarian cyst, treatment of endometriosis in the peritoneal cavity, and removing tissue from the external surface of the uterus.

2. A method for performing a gynecological procedure in the peritoneal cavity of a patient, the method comprising the steps of:
   a) inserting the distal end of a guidewire through the vagina, the cervix, the uterus, a fallopian tube, past a fimbria extending from a distal end of the fallopian tube toward an ovary, and into the peritoneal cavity;
   b) inserting the distal end of a scope distally over the guidewire until the distal end of the scope extends between the distal end of the fallopian tube, past the fimbria, and is positioned in the peritoneal cavity;
   c) removing the guidewire from the patient and from the scope, thereby leaving the guidewire lumen unoccupied;
   d) delivering a tool to the peritoneal cavity through the unoccupied lumen of the scope, the tool having at least a therapeutic utility; and
   e) using the tool to perform a therapeutic procedure on tissue in the peritoneal cavity, wherein the therapeutic procedure comprises at least one of draining an ovarian cyst, treatment of endometriosis in the peritoneal cavity, and removing a fibroid on the external surface of the uterus in the peritoneal cavity.

3. A method for performing a gynecological procedure in the peritoneal cavity of a patient, the method comprising the steps of:
   a) inserting the distal end of a guidewire through the vagina, the cervix, the uterus, a fallopian tube, past a fimbria extending from a distal end of the fallopian tube toward an ovary, and into the peritoneal cavity;
   b) inserting the distal end of a scope distally over the guidewire until the distal end of the scope extends between the distal end of the fallopian tube, past the fimbria, and is positioned in the peritoneal cavity;
   c) inserting the distal end of the guidewire through one of the uterus and the fornix;
   d) withdrawing the distal end of the guidewire from the patient through the vagina;
   e) delivering a tool to the peritoneal cavity by passing the tool over one of the proximal end of the guidewire and the distal end of the guidewire until the tool is positioned in the peritoneal cavity, the tool having at least one of a diagnostic utility and a therapeutic utility; and
   f) using the tool to perform at least one of draining an ovarian cyst, treatment of endometriosis in the peritoneal cavity, and removing a fibroid on the external surface of the uterus in the peritoneal cavity.

4. A method for accessing the peritoneal cavity of a patient according to claim 1, additionally comprising assessing the surface of the at least one of the fallopian tube and uterus with the scope.

5. A method for performing a gynecological procedure in the peritoneal cavity of a patient according to claim 2, wherein the step of using the tool to perform a therapeutic procedure comprises at least one of removing and ablating the tissue from a surface of at least one of the fallopian tube and uterus which is exposed to the peritoneal cavity.

6. A method for performing a gynecological procedure in the peritoneal cavity of a patient according to claim 2, wherein the step of using the tool to perform a therapeutic procedure comprises directing laser energy at a surface of at least one of the fallopian tube and uterus which is exposed to the peritoneal cavity.

7. A method for performing a gynecological procedure in the peritoneal cavity of a patient according to claim 3, wherein the step of using the tool to perform a therapeutic procedure comprises at least one of removing and ablating the tissue from a surface of at least one of the fallopian tube and uterus which is exposed to the peritoneal cavity.

8. A method for performing a gynecological procedure in the peritoneal cavity of a patient according to claim 3, wherein the step of using the tool to perform a therapeutic procedure comprises directing laser energy at a surface of at least one of the fallopian tube and uterus which is exposed to the peritoneal cavity.

* * * * *